United States Patent
Muranaka et al.

(10) Patent No.: US 8,969,654 B2
(45) Date of Patent: Mar. 3, 2015

(54) **TRITERPENE OXIDASE DERIVED FROM PLANT BELONGING TO GENUS *GLYCHYRRHIZA*, GENE ENCODING THE TRITERPENE OXIDASE, AND USE OF THE PROTEIN OR THE GENE**

(75) Inventors: Toshiya Muranaka, Yokohama (JP); Hikaru Seki, Yokohama (JP); Kiyoshi Ohyama, Yokohama (JP); Hiroshi Sudo, Sakura (JP); Satoru Sawai, Sakura (JP); Kazuki Saito, Chiba (JP)

(73) Assignee: Riken, Wako-shi (JP)

( * ) Notice: Subject to any disclaimer, the term of this patent is extended or adjusted under 35 U.S.C. 154(b) by 730 days.

(21) Appl. No.: 12/672,179

(22) PCT Filed: Aug. 6, 2008

(86) PCT No.: PCT/JP2008/064496
§ 371 (c)(1),
(2), (4) Date: Dec. 6, 2010

(87) PCT Pub. No.: WO2009/020231
PCT Pub. Date: Feb. 12, 2009

(65) Prior Publication Data
US 2011/0173724 A1    Jul. 14, 2011

(30) Foreign Application Priority Data
Aug. 6, 2007 (JP) .................................. 2007-204769

(51) Int. Cl.

| | | |
|---|---|---|
| *C07H 21/02* | (2006.01) | |
| *C07H 21/04* | (2006.01) | |
| *C12N 15/00* | (2006.01) | |
| *C12N 1/20* | (2006.01) | |
| *C12N 5/04* | (2006.01) | |
| *C12N 5/10* | (2006.01) | |
| *C12P 21/06* | (2006.01) | |
| *C12N 15/82* | (2006.01) | |
| *C12N 15/87* | (2006.01) | |
| *A01H 1/00* | (2006.01) | |
| *A61K 31/56* | (2006.01) | |
| *A61K 36/484* | (2006.01) | |
| *C07J 53/00* | (2006.01) | |
| *C12N 9/04* | (2006.01) | |

(52) U.S. Cl.
CPC ............. *A61K 31/56* (2013.01); *A61K 36/484* (2013.01); *C07J 53/00* (2013.01); *C12N 9/0006* (2013.01); *C12N 15/8243* (2013.01)
USPC .... 800/278; 536/23.1; 435/320.1; 435/252.3; 435/419; 435/69.1

(58) Field of Classification Search
USPC ........................................................ 800/278
See application file for complete search history.

(56) References Cited

U.S. PATENT DOCUMENTS

2003/0177518 A1* 9/2003 Osbourn et al. .............. 800/278
2004/0002105 A1   1/2004 Dixon et al.

FOREIGN PATENT DOCUMENTS

| JP | 2005-137291 | 6/2005 |
| WO | WO 03/093425 A2 | 11/2003 |
| WO | 2005 080572 | 9/2005 |

OTHER PUBLICATIONS

Friedberg, Automated protein function prediction—the genomic challenge, 7 Briefings in Bioinformatics, 225-242 at p. 231, top right column (2006).*
Ikuta et al., The Triterpenes from Stauntonia Hexaphylla Callus Tissues and Their Biosynthetic Significance, 52 Journal of Natural Products No. 3, 623-628 at 626, Right Column (1989).*
Shibuya et al. (Identification of β-amyrin and sophoradiol 24-hydroxylase by expressed sequence tag mining and functional expression assay, 273 FEBS Journal, 948-959 (2006).*
Suzuki et al. (A genomics approach to the early stages of triterpene saponin biosynthesis in *Medicago truncatula*, 32 Plant Journal, 1033-1048 (2002).*
Taylor, Triterpenes from *Salvia glutinosa* L., J. Chem. Soc. (C), 490 (1967).*
Ahamed et al., An artificial sweetener stimulates the sweet taste in insect: dual effects of Glycyrrhizin in *Phormia regina*, 26 Chem Senses, 507-515 at 507 (2001).*
Machine translation of JP 2005 137291 description retrieved from EPO website on Oct. 14, 2014.*
JP 2005 137291 bibliographic information retrieved from EPO website on Oct. 14, 2014.*
Shibuya, Masaaki et al., "Identification of β-amyrin and sophoradiol 24-hydroxylase by expressed sequence tag mining and funtional expression assay", The FEBS Journal, vol. 273, No. 5, pp. 948-959, (2006).
Seki, Hikaru et al., "Licorice β-amyrin 11-oxidase, a cytochrome P450 with a key role in the biosynthesis of the triterpene sweetener glycyrrhizin", PNAS, vol. 105, No. 37, pp. 14204-14209, (2008).
Extended European Search Report issued Jan. 20, 2012 in patent application No. 08792426.2.

(Continued)

*Primary Examiner* — Cynthia Collins
*Assistant Examiner* — Rebecca Coobs
(74) *Attorney, Agent, or Firm* — Oblon, McClelland, Maier & Neustadt, L.L.P.

(57) ABSTRACT

Provided is a protein having an activity of oxidizing a dammarane-type triterpene, a gene encoding the protein, and a method of using the protein and the gene. The protein can be obtained from a plant belonging to the genus *Glycyrrhiza*, which has an activity of oxidizing a dammarane-type triterpene. Also provided is a transformant producing a triterpene oxidase into which a gene encoding the triterpene oxidase is introduced.

14 Claims, 7 Drawing Sheets

(56) References Cited

OTHER PUBLICATIONS

Pimpimon Tansakul, et al., "Dammarenediol-II synthase, the first dedicated enzyme for ginsenoside biosynthesis, in *Panax ginseng*", FEBS Letters, vol. 580, No. 22, XP025232563, Oct. 2, 2006, pp. 5143-5149.

Hiroaki Hayashi, et al., "Cloning and Characterization of a cDNA Encoding β-Amyrin Synthase Involved in Glycyrrhizin and Soyasaponin Biosyntheses in Licorice", Biological & Pharmaceutical Bulletin, vol. 24, No. 8, XP002978733, Aug. 1, 2001, pp. 912-916.

U.S. Appl. No. 13/061,262, filed Feb 28, 2011, Muranaka, et al.

Extended European Search Report issued Jul. 3, 2012 in European Patent Application No. 09810081.1.

International Search Report issued Nov. 24, 2009 in PCT/JP2009/065197.

Hikaru Seki, et al., "Triterpene Functional Genomics in Licorice for Identification of CYP72A154 Involved in the Biosynthesis of Glycyrrhizin", The Plant Cell, vol. 23, No. 11, XP 002677792, Nov. 2011, pp. 4112-4123.

Lingyong Li, et al., "Genome-wide identification and characterization of putative cytochrome P450 genes in the model legume *Medicago truncatula*," Planta, vol. 226, Feb. 2, 2007, pp. 109-123.

Takahito Nomura, et al., "Cytochrome P450s in plant steroid hormone synthesis and metabolism," Phytochem Rev., vol. 5, Nov. 15, 2006, pp. 421-432.

Hikaru Seki, et al., "Triterpene Functional Genomics in Licorice for Identification of CYP72A154 Involved in the Biosynthesis of Glycyrrhizin", The Plant Cell, vol. 23, 2011, pp. 4112-4123.

\* cited by examiner

Fig. 1
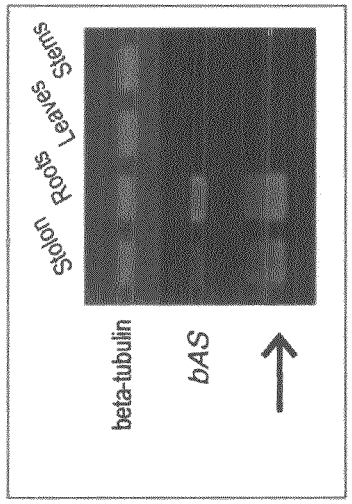
A
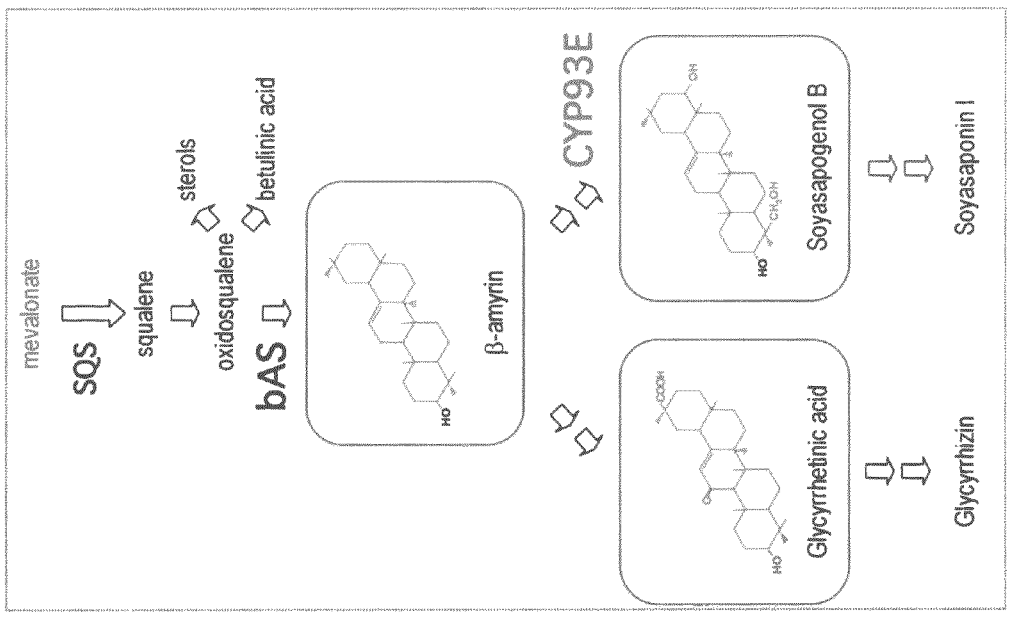
B

US 8,969,654 B2

TRITERPENE OXIDASE DERIVED FROM PLANT BELONGING TO GENUS *GLYCHYRRHIZA*, GENE ENCODING THE TRITERPENE OXIDASE, AND USE OF THE PROTEIN OR THE GENE

TECHNICAL FIELD

The present invention relates to an enzyme which oxidizes a dammarane-type triterpene derived from a plant belonging to the genus *Glychyrrhiza*, a gene encoding the same, and use of the enzyme and the gene.

BACKGROUND ART

Plants belonging to the genus *Glychyrrhiza* are perennial herbaceous plants belonging to the family Fabaceae. Among raw materials for Chinese herbal medicines, underground roots and stolons of plants belonging to the genus *Glychyrrhiza* are important ones, and they are widely used for pharmaceuticals worldwide. A main active ingredient of the plants belonging to the genus *Glychyrrhiza, Glychyrrhiza uralensis, Glychyrrhiza glabra*, and *Glychyrrhiza inflata* is glycyrrhizin, which is a triterpene saponin. Numerous studies have been conducted on glycyrrhizin from various perspectives such as pharmacognostic study, pharmacological study, and breeding study. Yet, regarding the biosynthetic pathway of glycyrrhizin, it has been absolutely unknown how glycyrrhizin is biosynthesized following β-amyrin, which is a triterpene. In order to stably and continuously supply a good quality herbal medicine, establishment of optimal conditions for production, selection of a high-production strain, and the like are necessary using a biosynthesis gene itself of glycyrrhizin, which is an active ingredient, or a gene expression thereof as a marker. However, such an approach has not been able to be implemented because the biosynthetic pathway is unknown. Also, molecular breeding of a plant producing a large amount of glycyrrhizin by introduction of the biosynthesis gene has not been able to be realized.

The biosynthesis pathway of soyasapogenol B from β-amyrin has been well studied, and CYP93E (FIG. 1), a gene encoding an enzyme which hydroxylates β-amyrin at the position 24, is disclosed in International Publication WO/2005/080572 and by Shibuya et al. in Identification of beta-amyrin and sophoradiol 24-hydroxylase by expressed sequence tag mining and functional expression assay., FEBS J. 2006 March; 273(5): 948-59.

DISCLOSURE OF THE INVENTION

Problems targeted by the present invention are to identify a protein having an activity of oxidizing a dammarane-type triterpene and a gene encoding the same, and to provide the protein and the gene as well as use of the protein and the gene.

The present inventors devoted a full effort to solve the aforementioned problems, and as a result, they successfully isolated a novel cytochrome P450 gene (hereinafter called P450 gene) having such a catalytic function as to oxidize a carbon at the position 11 of a dammarane-type triterpene such as β-amyrin, thereby completing the present invention.

The present invention is summarized as follows.
(1) A protein having an activity of oxidizing a carbon at the position 11 of a dammarane-type triterpene.
(2) The protein according to (1), wherein the dammarane-type triterpene is β-amyrin or 30-hydroxy-β-amyrin.
(3) The protein according to (1) or (2), being derived from a plant belonging to the genus *Glychyrrhiza*.
(4) The protein according to (3), wherein the plant belonging to the genus *Glychyrrhiza* is *Glychyrrhiza uralensis* or *Glychyrrhiza glabra*.
(5) The protein according to any one of (1) to (4), comprising any one of amino acid sequences as shown in (a) to (c) below:
(a) the amino acid sequence shown in SEQ ID NO:1;
(b) an amino acid sequence comprising a deletion(s), substitution(s), or addition(s) of one or several amino acids in the amino acid sequence shown in SEQ ID NO:1; and
(c) an amino acid sequence having an 80% or more identity with the amino acid sequence shown in SEQ ID NO:1.
(6) The protein according to any one of (1) to (5), comprising an amino acid sequence shown in SEQ ID NO:2 or SEQ ID NO:13.
(7) A gene encoding a protein having an activity of oxidizing a carbon at the position 11 of a dammarane-type triterpene.
(8) The gene according to (7), wherein the dammarane-type triterpene is β-amyrin or 30-hydroxy-β-amyrin.
(9) The gene according to (7) or (8), being derived from a plant belonging to the genus *Glychyrrhiza*.
(10) The gene according to (9), wherein the plant belonging to the genus *Glychyrrhiza* is *Glychyrrhiza uralensis* or *Glychyrrhiza glabra*.
(11) The gene according to any one of (7) to (10), comprising any one of nucleotide sequences as shown in (d) to (g) below:
(d) the nucleotide sequence shown in SEQ ID NO:3;
(e) a nucleotide sequence comprising a deletion(s), substitution(s), or addition(s) of one or several nucleotides in the nucleotide sequence shown in SEQ ID NO:3;
(f) a nucleotide sequence having an 80% or more identity with the nucleotide sequence shown in SEQ ID NO:3; and
(g) a nucleotide sequence hybridizing with a nucleotide sequence complementary to the nucleotide sequence shown in SEQ ID NO:3 under stringent conditions.
(12) The gene according to any one of (7) to (11), comprising a nucleotide sequence shown in SEQ ID NO:4 or SEQ ID NO:14.
(13) A recombinant vector containing the gene according to any one of (7) to (12).
(14) A transformant containing the gene according to any one of (7) to (12) or the recombinant vector according to (13).
(15) The transformant according to (14), being a plant belonging to the genus *Glychyrrhiza*.
(16) The transformant according to (15), wherein the plant belonging to the genus *Glychyrrhiza* is *Glychyrrhiza uralensis* or *Glychyrrhiza glabra*.
(17) The transformant according to any one of (14) to (16), wherein expression of the gene according to any one of (7) to (12) is enhanced.
(18) The transformant according to any one of (14) to (16), wherein expression of the gene according to any one of (7) to (12) is suppressed.
(19) A method for producing the protein according to any one of (1) to (6), comprising culturing or growing the transformant according to any one of (14) to (17) and collecting the protein according to any one of (1) to (6) from the obtained culture or grown product.
(20) A method for oxidizing a dammarane-type triterpene, comprising acting the protein according to any one of (1) to (6) on a dammarane-type triterpene.
(21) A method for selecting a plant by determining the presence or absence, or expression, of the gene according to any one of (7) to (12) in a plant, comprising detecting or quantitating the gene by conducting a PCR method, a RT- PCR method, or nucleic acid hybridization using the gene or a fragment thereof in a sample containing a nucleic acid prepared from the plant.

The present invention encompasses contents described in the specification and/or figures in JP Patent Application No. 2007-204769, based on which the present application claims a priority.

BRIEF DESCRIPTION OF THE DRAWINGS

FIG. 1A shows biosynthetic pathways of glycyrrhizin and soyasaponin I, and FIG. 1B shows results of gene expression analysis by a RT-PCR method.

BEST MODE FOR CARRYING OUT THE INVENTION

Figure 2:
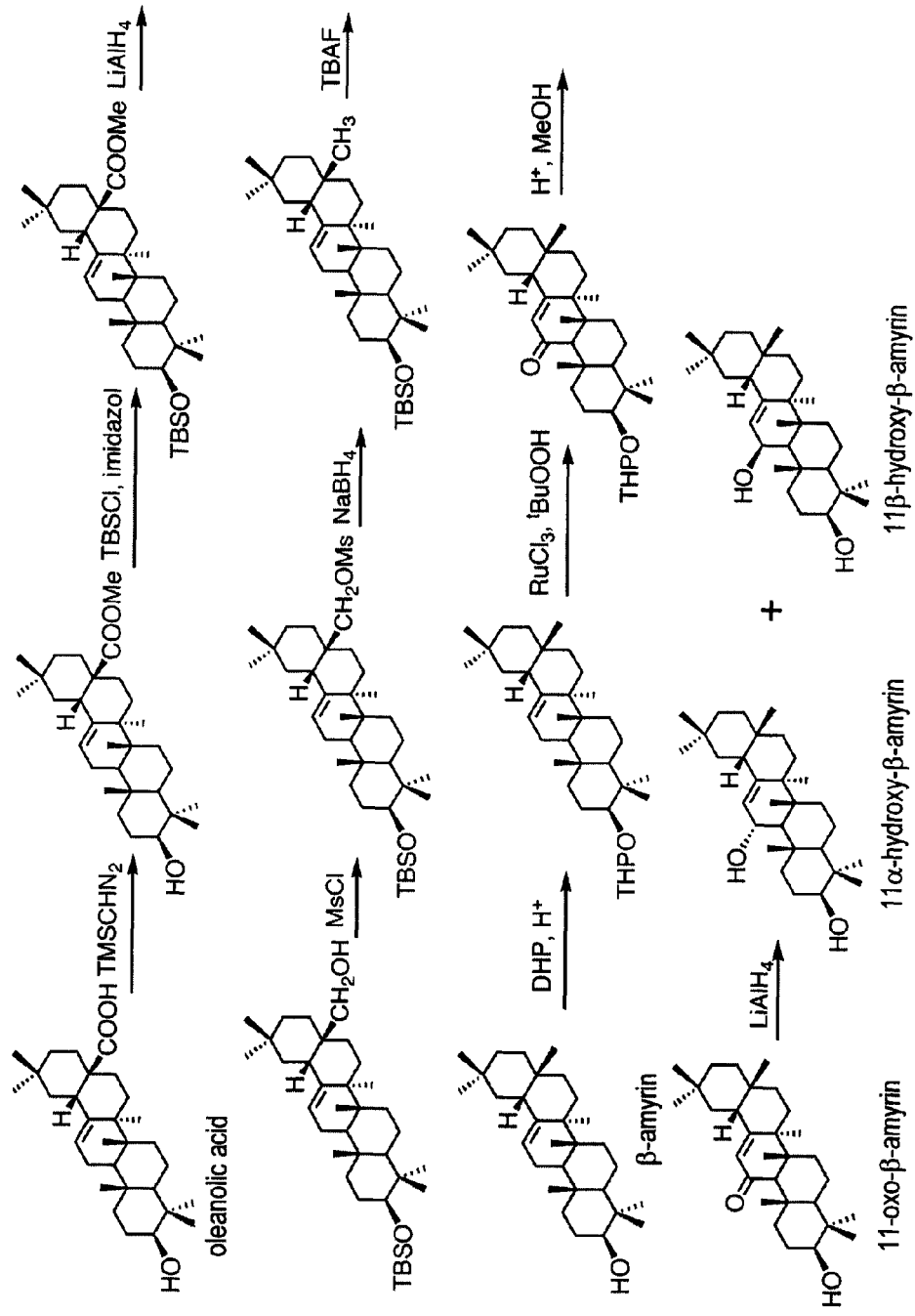
FIG. 2 shows a method for synthesizing a triterpenoid.

The present invention is described in detail hereinbelow.

(1) Protein of the Present Invention

The protein of the present invention is a triterpene oxidase having an activity of oxidizing a carbon at the position 11 of a dammarane-type triterpene. A dammarane-type triterpene refers to a group of compounds produced from dammarene cations, in which 2,3-oxidosqualene is cyclized in a chair-chair-chair-boat conformation, and examples thereof include a tetracyclic compound and a pentacyclic compound. Specific examples of the dammarane-type triterpene include dammarane-type, limonoid-type, quassinoid-type, lupane-type, oleanane-type, and ursane-type triterpenes. Although the dammarane-type triterpene is not particularly limited in the present invention, it is preferably an oleanane-type triterpene. Examples of the oleanane-type triterpene include β-amyrin, oleanolic acid, hederagenin, 11-deoxoglycyrrhetinic acid, camelliagenin, soyasapogenol, and saikogenin. Although no particular limitation is imposed, the oleanane-type triterpene is preferably β-amyrin and 30-hydroxy-β-amyrin.

Examples of the protein of the present invention include;

(a) a protein having the amino acid sequence shown in SEQ ID NO:1;

(b) a protein having an amino acid sequence comprising a deletion(s), substitution(s), or addition(s) of one or several amino acids in the amino acid sequence shown in SEQ ID NO:1, and an activity of oxidizing a carbon at the position 11 of a dammarane-type triterpene; or (c) a protein having an amino acid sequence having an 80% or more identity with the amino acid sequence shown in SEQ ID NO:1 and an activity of oxidizing a carbon at the position 11 of a dammarane-type triterpene.

The protein having the amino acid sequence shown in SEQ ID NO:1 refers to a protein encoded by a gene (SEQ ID NO:3) obtained from stolons of a plant belonging to the genus Glychyrrhiza (Glychyrrhiza uralensis).

In the present invention, the phrase "an amino acid sequence comprising a deletion(s), substitution(s), or addition(s) of one or several amino acids in the amino acid sequence shown in SEQ ID NO:1" means that, for example, one to ten amino acid(s), preferably one to five amino acid(s), may be deleted from the amino acid sequence shown in SEQ ID NO:1, and one to ten amino acid(s), preferably one to five amino acid(s), may be added to the amino acid sequence shown in SEQ ID NO:1, or one to 10 amino acid(s), preferably one to five amino acid(s) in the amino acid sequence shown in SEQ ID NO:1 may be substituted by other amino acid(s).

Examples of the above-described amino acid sequence include the amino acid sequences shown in SEQ ID NO:2 and SEQ ID NO:13. The amino acid sequences shown in SEQ ID NO:2 and SEQ ID NO:13 each differ at four and seven amino acids, respectively, in comparison with the amino acid sequence shown in SEQ ID NO:1. Further, proteins having the amino acid sequences shown in SEQ ID NO:2 and SEQ ID NO:13 are each encoded by genes having the nucleotide sequences of SEQ ID NO:4 and SEQ ID NO:14, respectively.

Furthermore, in the present invention, the "identity" in "an amino acid sequence having an 80% or more identity with the amino acid sequence shown in SEQ ID NO:1" is 80% or more, preferably 85% or more, more preferably 90%, and even more preferably 95% or more.

Although an origin of the protein of the present invention is not particularly limited, it is preferably a plant belonging to the genus Glychyrrhiza, and more preferably Glychyrrhiza uralensis or Glychyrrhiza glabra.

The plant belonging to the genus Glychyrrhiza in the present invention is a plant which is classified into the genus Glychyrrhiza in the family Fabaceae. Such a plant can be exemplified by Glychyrrhiza glabra, Glychyrrhiza inflata, Glychyrrhiza uralensis, Glychyrrhiza aspera, Glychyrrhiza eurycarpa, Glychyrrhiza pallidiflora, Glychyrrhiza yunnanensis, Glychyrrhiza lepidota, Glychyrrhiza echinata, and Glychyrrhiza acanthocarpa. Among them, it has been reported that glycyrrhizin was detected in Glychyrrhiza glabra, Glychyrrhiza inflata, and Glychyrrhiza uralensis.

While the protein of the present invention can be obtained from, for example, stolons or roots of a plant belonging to the genus Glychyrrhiza by using publicly known methods, a protein having the amino acid sequence shown in SEQ ID NO:1, 2, or 13 can be synthesized by publicly known chemical synthesis methods, or the protein of the present invention can be produced by obtaining a gene encoding the protein, which will be described later, and applying publicly known gene recombination techniques.

Further, an amino acid sequence comprising a deletion(s), substitution(s), or addition(s) of one or several amino acids in the amino acid sequence shown in SEQ ID NO:1, or an amino acid sequence having an 80% or more identity with the amino acid sequence shown in SEQ ID NO:1 can be obtained by, for example, modifying a gene described below with techniques publicly known in the art. Introduction of a mutation in a gene can be conducted by using a publicly known technique such as the Kunkel method or the Gapped duplex method, or in accordance with such method. For example, a mutation can be introduced by using a kit for introducing a mutation employing a site-directed mutagenesis method (for example, Mutant-K (a product of Takara Shuzo Co., Ltd.) and Mutant-G (a product of Takara Shuzo Co., Ltd.)), or a LA PCR in vitro Mutagenesis series kit (a product of Takara Shuzo Co., Ltd.) Also, a method in which a gene is contacted with a mutagen, and a method of irradiating ultraviolet, and the like can be employed.

The protein of the present invention can be employed in a method for oxidizing a dammarane-type triterpene. For example, when the protein of the present invention acts on β-amyrin, which is a substrate for the protein, a carbon at the position 11 of the β-amyrin is oxidized. Substance obtainable by above oxidation are 11α-hydroxy-β-amyrin and 11-oxo-β-amyrin for example. Also, when the protein of the present invention acts on 30-hydroxy-β-amyrin, which is a substrate for the protein, a carbon at the position 11 of the 30-hydroxy-β-amyrin is oxidized. Substance obtainable by above oxidation are 11α,30-dihydroxy-β-amyrin and 30-hydroxy-11-oxo-β-amyrin for example.

(2) Gene of the Present Invention

The gene of the present invention encodes a protein having an activity of oxidizing a carbon at the position 11 of a dammarane-type triterpene.

The present inventors prepared mRNA from stolons of a plant belonging to the genus *Glychyrrhiza* and produced a cDNA library to conduct EST analysis. Based on the presumption that P450 gene is involved in the pathway to biosynthesize glycyrrhizin (also called glycyrrhizic acid) from β-amyrin through multiple steps of oxidation, glycosylation, and the like, the present inventors conducted a search using the nucleotide sequence of a publicly known P450 gene in order to narrow down a candidate gene. The present inventors analyzed the expression of the candidate gene, thereby identifying the gene of the present invention (see Examples described below).

Examples of the Gene of the Present Invention Include;

(d) the nucleotide sequence shown in SEQ ID NO:3;

(e) a nucleotide sequence comprising a deletion(s), substitution(s), or addition(s) of one or several nucleotides in the nucleotide sequence shown in SEQ ID NO:3, which encodes a protein having an activity of oxidizing a carbon at the position 11 of a dammarane-type triterpene;

(f) a nucleotide sequence having an 80% or more identity with the nucleotide sequence shown in SEQ ID NO:3, which encodes a protein having an activity of oxidizing a carbon at the position 11 of a dammarane-type triterpene; or (g) a nucleotide sequence which hybridizes with a nucleotide sequence complementary to the nucleotide sequence shown in SEQ ID NO:3 under stringent conditions, and which encodes a protein having an activity of oxidizing a carbon at the position 11 of a dammarane-type triterpene.

In the present invention, the phrase "a nucleotide sequence comprising a deletion(s), substitution(s), or addition(s) of one or several nucleotides in the nucleotide sequence shown in SEQ ID NO:3" means that, for example, one to ten nucleotide(s), preferably one to five nucleotide(s), can be deleted from the nucleotide sequence shown in SEQ ID NO:3, and one to ten nucleotide(s), preferably one to five nucleotide(s), can be added to the nucleotide sequence shown in SEQ ID NO:3, and one to ten nucleotide(s), preferably one to five nucleotide(s), in the nucleotide sequence shown in SEQ ID NO:3 can be substituted by other nucleotide(s).

In the present invention, the "identity" in "a nucleotide sequence having an 80% or more identity with the nucleotide sequence shown in SEQ ID NO:3" is 80% or more, preferably 85% or more, more preferably 90%, and even more preferably 95% or more.

An example of the above-described gene includes, for example, a gene having the nucleotide sequence shown in SEQ ID NO:4. The nucleotide sequence shown in SEQ ID NO:4 differs at 11 nucleotides in comparison with the nucleotide sequence shown in SEQ ID NO:3. Furthermore, an example of the above-described gene includes a gene having the nucleotide sequence shown in SEQ ID NO:14, which is derived from *Glychyrrhiza glabra*. The nucleotide sequence shown in SEQ ID NO:14 differs at 14 nucleotides in comparison with the nucleotide sequence shown in SEQ ID NO:3.

In the present invention, the "stringent conditions" refers to such conditions under which a so-called specific hybrid is formed, while a non-specific hybrid is substantially not formed. An example of such conditions includes conditions under which a complementary strand of a highly identical nucleic acid, namely, a DNA composed of a nucleotide sequence having an 80% or more, preferably an 85% or more, more preferably a 90% or more, and even more preferably a 95% or more identity with the nucleotide sequence shown in SEQ ID NO:3, hybridizes, while a complementary strand of a nucleic acid less identical than the above does not hybridizes. More specifically, such conditions refer to conditions in which the sodium salt concentration is 15 to 750 mM, preferably 50 to 750 mM, and more preferably 300 to 750 mM, the temperature is 25 to 70° C., preferably 50 to 70° C., and more preferably 55 to 65° C., and the formamide concentration is 0 to 50%, preferably 20 to 50%, and more preferably 35 to 45%. Furthermore, under stringent conditions, conditions for washing a filter after hybridization normally comprise the following: the sodium salt concentration is 15 to 600 mM, preferably 50 to 600 mM, and more preferably 300 to 600 mM, and the temperature is 50 to 70° C., preferably 55 to 70° C., and more preferably 60 to 65° C.

The gene of the present invention can be isolated from a plant belonging to the genus *Glychyrrhiza* using publicly known methods. The gene of the present invention can be obtained as a nucleic acid fragment by conducting PCR amplification using a nucleic acid derived from a cDNA library or a genomic DNA library or the like as a template along with primers designed based on the nucleotide sequence shown in SEQ ID NO:3, SEQ ID NO:4, or SEQ ID No:14. Also, the gene of the present invention can be obtained as a nucleic acid fragment by carrying out hybridization using a nucleic acid derived from the aforementioned libraries as a template, and employing a fragment, which is a part of the gene, as a probe. Alternatively, the gene of the present invention can be synthesized by a publicly known nucleic acid sequence synthesis method such as a chemical synthesis method.

Furthermore, a nucleotide sequence comprising a deletion(s), substitution(s), or addition(s) of one or several nucleotides in the nucleotide sequence shown in SEQ ID NO:3, or a nucleotide sequence having an 80% or more identity with the nucleotide sequence shown in SEQ ID NO:3 can be produced by introducing a mutation using the above-described methods, and the like.

(3) Recombinant Vector of the Present Invention

The recombinant vector of the present invention can be constructed by introducing the above-described gene into an appropriate vector. The kind of the vector is not particularly limited, and pBI-based, pPZP-based, pSMA-based, pUC-based, pBR-based, pBluescript, pKS1, pTriEX™-based (a product of Takara Shuzo Co., Ltd.) vectors and the like can be used. Also, a virus vector such as a cauliflower mosaic virus (CaMV), a bean golden mosaic virus (BGMV), and a tobacco mosaic virus (TMV) can also be used. Also, a binary vector such as a pBI-based vector can be used.

In order to insert a gene of interest into a vector, a method in which a purified DNA is cleaved by an appropriate restriction enzyme(s) and connecting the DNA thus obtained to an appropriate vector DNA by inserting it into a restriction site or a multicloning site of the vector, and the like are employed.

Also, besides a gene of interest, for example a promoter, an enhancer, a terminator, a selection marker gene, and the like can be connected. Further, a β-amyrin-synthase gene can be contained.

Examples of a promoter operable in a plant cell include a cauliflower mosaic virus (CaMV) 35S promoter, a promoter of a nopaline-synthase gene (Pnos), a ubiquitin promoter derived from corn, an actin promoter derived from rice, and a PR protein promoter derived from tobacco. Also, examples of a promoter operable in a bacterial cell include a promoter of a *Bacillus stearothermophilus* maltogenic amylase gene, a *Bacillus licheniformis* α-amylase gene, a *Bacillus amyloliquefaciens* BAN amylase gene, a *Bacillus subtilis* alkaline protease gene, or a *Bacillus pumilus* xylosidase gene, or a $P_R$ or $P_L$ promoter of a phage λ, and a lac, trp, or tac promoter of an *Escherichia coli*. Examples of a promoter operable in a yeast host cell include a promoter derived from a gene involved in a yeast glycolysis system, an alcohol dehydrogenase gene promoter, a TPI 1 promoter, and an ADH2-4c promoter. Examples of a promoter operable in a fungus include an ADH3 promoter and a tpiA promoter. Examples of a promoter operable in an animal cell include a SV40 early promoter, a SV 40 late promoter, and a CMV promoter, and examples of a promoter operable in an insect cell include a polyhedrin promoter, a P10 promoter, an autographa californica polyhedrosis basic protein promoter, a baculovirus immediate early gene 1 promoter, and a baculovirus 39K delayed-early gene promoter.

Examples of an enhancer include an enhancer region in a CaMV 35S promoter containing an upstream sequence, a SV40 enhancer, and a CMV enhancer.

Examples of a terminator include a terminator of a nopaline-synthase (NOS) gene, a terminator of an octopine-synthase (OCS) gene, a CaMV 35S terminator, a 3' terminator of an *Escherichia coli* lipopolyprotein 1 pp, trp operon terminator, amyB terminator, and a terminator of an ADH1 gene.

Examples of a selection marker gene include a drug resistance gene (such as a tetracycline resistance gene, an ampicillin resistance gene, a kanamycin resistance gene, a hygromycin resistance gene, a spectinomycin resistance gene, a chloramphenicol resistance gene, or a neomycin resistance gene), a fluorescent or luminescent reporter gene (such as a luciferase, a β-galactosidase, a β-glucuronidase (GUS), or a green fluorescent protein (GFP)), and an enzyme gene such as a neomycin phosphotransferase II (NPT II) or a dihydrofolate reductase.

(4) Transformant of the Present Invention

The transformant of the present invention can be produced by introducing the above-described gene or recombinant vector into an appropriate host.

A host is not limited insofar as an introduced gene can be expressed, and it can be a bacterium such as *Escherichia coli* or *Bacillus subtilis*, a yeast such as *Saccharomyces cerevisiae, Saccharomyces pombe,* or *Pichia pastoris*, a fungus such as *Aspergillus, Neurospora, Fusarium,* or *Trichoderma*, or a monocotyledonous or dicotyledonous plant, for example, a plant belonging to the family Fabaceae, the family Brassicaceae, or the like, a plant cell, or an animal cell, or an insect cell such as sf9 and sf21.

Examples of introduction of a gene or a recombinant vector include a publicly known method, for example, an *Agrobacterium* method, a PEG-calcium phosphate method, an electroporation method, a liposome method, a particle gun method, and a microinjection method. An introduced gene can be incorporated into a host genome DNA or present in the form of being contained in an exogenous vector.

Upon introduction of the gene or recombinant vector of the present invention into a host in accordance with the above-described methods, whether or not the gene has been incorporated in the host can be confirmed. Such a confirmation can be carried out by a PCR method, a Southern hybridization method, a Northern hybridization method, in situ hybridization, and the like.

Furthermore, a transformant in which expression of the gene of the present invention is enhanced can be provided by introducing the gene or recombinant vector of the present invention in such a way that it can be expressed. Therefore, according to the present invention, a transformant which produces an increased amount of glycyrrhizin in association with an enhanced expression of the gene of the present invention can also be provided.

When a transformant is a plant, it is preferably a plant belonging to the family Fabaceae, particularly a plant belonging to the genus *Glychyrrhiza* (including *Glychyrrhiza uralensis, Glychyrrhiza glabra,* or *Glychyrrhiza inflata*). The "plant" as used in the present invention includes a plant body, a plant organ, a plant tissue, a plant cell, a culture of these plant parts, and a seed, and the "transformant" includes a transformed plant produced by genetic engineering and progeny thereof. Examples of a subject to be transformed include a plant body, a plant tissue (including, for example, an epidermis, a phloem, a parenchyma, a xylem, a vascular bundle, or a plant organ (for example, leave, petal, stem, root, or seed)), or plant cells, and no particular limitation is imposed thereon.

A tumor tissue, a shoot, a hairy root, and the like obtained as a result of transformation can be employed in cell culture, tissue culture, or organ culture without modification, or, they can be regenerated into a plant body by, for example, administration of an appropriate concentration of a plant hormone (such as auxin, cytokinin, gibberellin, abscisic acid, ethylene, and brassinolide) and the like using a conventionally known plant tissue culture method. Regeneration of a plant body is generally conducted by differentiating a root on a medium in which appropriate kinds of auxin and cytokinin are mixed and transplanting it to a medium having cytokinin in abundance to differentiate a shoot, and subsequently transplanting it to hormone-free soil.

Furthermore, a transformant in which expression of the gene of the present invention is suppressed can be provided. Such a transformant can be employed, for example, in a research for revealing the glycyrrhizin biosynthesis pathway. Suppression of the expression of the gene of the present invention includes suppression of transcription of the gene and suppression of translation into a protein, and it includes complete silencing of the gene expression as well as reduction in the expression. An expression of the gene can be disabled or suppressed when the gene is artificially or naturally mutated or destroyed, or by employing various genetic engineering techniques such as a RNA interference method, an antisense method, a ribozyme method, a co-suppression method, and a method to control a transcription factor.

(5) Method for Producing the Protein of the Present Invention

The protein of the present invention can be produced by culturing or growing a host in an appropriate medium under such conditions by which an introduced gene can be expressed, and the conditions depend on a host.

When the protein of the present invention is produced by culturing a host, examples of a medium include, for example, a LB medium, a M9 medium, a YPD medium, a YPG medium, a YPM medium, a YPDM medium, and a SMM medium, and the medium appropriately contains a carbon source(s) (for example, glucose, glycerin, mannitol, fructose, and lactose), a nitrogen source(s) (for example, an inorganic nitrogen such as ammonium sulfate and ammonium chloride, an organic nitrogen such as a casein degradation product, a yeast extract, polypeptone, bacto tryptone, and a beef extract), inorganic salts (for example, diphosphate sodium, diphosphate potassium, magnesium chloride, magnesium sulfate, and calcium chloride), vitamins (such as vitamin B1), and a drug agent (an antibiotic such as ampicillin, tetracycline, or kanamycin). Furthermore, a dammarane-type triterpene, preferably an oleanane-type triterpene, more preferably β-amyrin, which serves as a substrate for the protein of the present invention, can be added to the medium.

Although no particular limitation is imposed on a culture condition as long as it is suitable for expression of a gene, culturing is normally conducted at 10 to 45° C. for several hours to several hundred hours with aeration and stirring as needed.

In order to collect the protein of the present invention from a culture (including a culture supernatant and a cultured transformant), a protein accumulated in the culture can be extracted by a publicly known method, and then purified as needed. The protein of the present invention can be obtained by, for example, employing a solvent extraction method, a salting-out method, a solvent precipitation method, a dialysis method, an ultrafiltration method, a gel electrophoresis method, a gel filtration chromatography, an ion exchange chromatography, a reverse phase chromatography, and an affinity chromatography, either alone or in combination as appropriate.

It is to be noted that when the transformant is cultured in a medium into which a dammarane-type triterpene such as the above-described β-amyrin which serves as a substrate for the protein of the present invention has been added, a derivative in which a carbon at the position 11 of the dammarane-type triterpene is oxidized can be obtained.

When the protein of the present invention is produced by growing a transformed plant and the like, the protein of the present invention is extracted from a regenerated plant body or the like by the above-described publicly known method, and purified as needed. Also, in a case of a plant belonging to the genus *Glychyrrhiza*, the protein of the present invention is contained in stolons and roots in abundance, and the above-described derivatived or glycyrrhizin produced via the biosynthetic pathway of glycyrrhizin can be collected from stolons and roots.

(6) Plant Selection Method Using the Gene of the Present Invention

A method for selecting a plant by determining the presence or absence, or expression, of the gene of the present invention in a plant, comprises detecting or quantitating the gene of the present invention by conducting a PCR method, a RT-PCR method, or nucleic acid hybridization using the gene of the present invention or a fragment thereof in a sample containing a nucleic acid prepared from the aforementioned plant.

A sample containing a nucleic acid of a plant can be prepared using a publicly known method, for example, a phenol extraction method, a phenol-chloroform extraction method, or a CTAB method.

Presence or absence, or expression, of the gene of the present invention can be detected or quantitated by a PCR (polymerase chain reaction) method, a RT-PCR (reverse transcription-polymerase chain reaction) method, or a nucleic acid hybridization method. Examples of a nucleic acid hybridization method include, for example, DNA-DNA hybridization, DNA-RNA hybridization, or RNA-RNA hybridization, and for example, Northern hybridization (see Bunshiseibutsugaku jikken protocol I (Short Protocols in Molecular Biology) (1997), joint translation by NISHINO and SANO, Maruzen Co., Ltd.), and a DNA microarray method (see DNA microarray to saishin PCR ho (DNA microarray and the latest PCR method) (2000), MURAMATSU, edited by NAWA, Shujunsha Co., Ltd.) can be employed.

A primer or a probe used in a PCR method, a RT-PCR method, or nucleic acid hybridization can be designed using a gene having a nucleotide sequence of any one of (d) to (g) described above or a fragment thereof.

A "fragment" as used in the present invention refers to a fragment composed of a consecutive nucleotide sequence of 10 nucleotides at a minimum, 15 nucleotides, 20 nucleotides, 25 nucleotides, 30 nucleotides, 50 nucleotides, 100 nucleotides, or 150 nucleotides of the above-described nucleotide sequences.

Although no particular limitation is imposed on a size of a primer or a probe to be used in the present invention, in a case of a primer, it is normally approximately 15 to approximately 50 base-long, preferably approximately 17 to approximately 30 base-long. In a case of a probe, it is at least approximately 10 base-long or more to a full length, preferably approximately 15 base-long or more to a full length, more preferably approximately 30 base-long or more to a full length, and even more preferably approximately 50 base-long or more to a full length in Northern hybridization. In DNA microarray, a probe of approximately 10 to approximately 50 base-long, preferably a probe of approximately 15 to approximately 30 base-long, and more preferably a probe of approximately 20 to approximately 25 base-long is used; however, a size is not limited to the above description. In general, the longer the probe is, the better the efficiency of hybridization is, and the higher the sensitivity becomes. In contrast, the shorter the probe is, the lower the sensitivity is, while the higher the specificity becomes. A probe is spotted on a solid phase normally with a solution of 0.1 μg to 0.5 μg. Examples of a primer and a probe include, for example, SEQ ID NO:5 and SEQ ID NO:6, while no particular limitation is imposed thereon.

Conditions of PCR include, for example, carrying out denaturation of DNA at 94 to 95° C. for five seconds to five minutes, annealing of a primer at 50 to 70° C. for 10 seconds to one minute, and an extension reaction at 68 to 72° C. for 30 seconds to 3 minutes as one cycle, and performing the above cycle for approximately 15 to 40 cycles, followed by an extension reaction at 68 to 72° C. for 30 seconds to 10 minutes in the end.

A PCR product can be detected by using, for example, agarose electrophoresis, polyacrylamide gel electrophoresis, or dot hybridization.

An example of a method for quantitating an expression level of the gene of the present invention by a PCR method includes a RT-PCR method employing an internal standard substance (see PCR ho saizensen (Recent Advances in PCR Methodology) (1996), edited by SEKIYA and FUJINAGA, Kyoritsu Shuppan Co., Ltd.) A housekeeping gene is frequently employed as an internal standard to be used. In this method, a comparative result revealing whether an amount of a target mRNA is larger or smaller with respect to an internal standard sample is obtained. While a PCR reaction is conducted on one sample, a reaction liquid is sampled every a few cycles to quantitate an amount of PCR product, and values thus obtained are plotted on a graph. A regression analysis is performed with respect to a point of an exponential amplification phase on the graph thus obtained to find y-intercept, thereby an initial amount of a template can be calculated (Bio jikken illustrated (Biological experiment illustrated) 3, "honto ni fueru PCR (truly productive PCR)" (1998), written by NAKAYAMA, Hiroki, Shujunsha Co., Ltd.)

Also, an expression level of the gene of the present invention can be quantitated by a RT-PCR method. When a PCR reaction is carried out in a reaction system in which a PCR product is specifically fluorescently-labeled by a thermal cycler instrument equipped with a device which detects a fluorescence intensity, an amount of a product in the reaction can be monitored in real time without requiring sampling, and results thus obtained are subjected to regression analysis on a computer. Examples of a method for labeling a PCR product include a method employing a fluorescently-labeled probe and a method employing a reagent which specifically binds to a double-stranded DNA. Once a PCR reaction is conducted, a probe is degraded by a 5'→3' exonuclease activity of a Taq polymerase and then emits florescence. The amount of fluorescence thus observed reflects an amount of a PCR product. Given that the number of cycle needed for a PCR reactant to reach a detection limit ($C_T$) and an initial amount of a template are inversely correlated, an initial amount of a template is quantitated by measuring $C_T$ in a real-time measurement method. If $C_T$ is measured using multiple levels of known amounts of templates and a calibration curve is produced, an absolute value of an initial amount of a template of an unknown sample can be calculated. Examples of reverse transcriptase used in a RT-PCR include, for example, M-MLV RTase and ExScript RTase (products of Takara Bio Inc.), and Super Script II RT (a product of GIBCO-BRL).

When nucleic acid hybridization is performed, a probe, or a nucleic acid in a sample can be labeled with any of an isotope (for example, $^{32}P$, $^{33}P$, and $^{35}S$) or a fluorescein (fluorescamine or a derivative thereof, rhodamine or a derivative thereof, FITC, Cy3, or Cy5), and no particular limitation is imposed thereon.

Also, hybridization is preferably performed under the above-described stringent conditions.

A Northern hybridization method is generally used for detection and quantitation of a RNA sequence. A RNA sample obtained from a plant by a publicly known method is subjected to agarose gel electrophoresis to be separated by size, and subsequently the RNA thus separated is transferred to a nylon or nitrocellulose membrane. Then, hybridization is performed using labeled cDNA of the gene of the present invention or a fragment thereof as a probe to detect and quantitate the gene of the present invention.

In a DNA microarray method, cDNA encoding the gene of the present invention, or a sense strand or an antisense strand thereof, or fragments of these DNA are immobilized on an array such as a glass or a filter, as a probe. A reverse transcription reaction is performed on RNA obtained by a publicly known method, and Cy3-dUTP, Cy5-dUTP, and the like are allowed to be taken up during the reaction, thereby labeled cDNA is provided. Then, hybridization of the probe immobilized on an array with the labeled cDNA is performed to detect and quantitate the gene of the present invention. A plant with a high content of glycyrrhizin can be thus selected and screened.

It is to be noted that Sambrook, J. et. al., (1989) Molecular Cloning: a Laboratory Manual Second Ed., Cold Spring Harbor Laboratory Press, Cold Spring Harbor, N.Y. can be referred to for experimental methods associated with the above-described molecular biological techniques.

The present invention is described in detail hereinbelow based on Examples; however, these Examples are not intended to limit the present invention.

Example 1

Preparation of mRNA from a Plant Belonging to the Genus *Glychyrrhiza* and Production of a cDNA Library (1)

A stolon (underground stem) of seven-year-old *Glychyrrhiza uralensis* cultivated in a field at Research Center for Medicinal Plant Resources, Hokkaido Division (Nayoro city, Hokkaido), of National Institute of Biomedical Innovation was harvested in June. A total RNA was prepared therefrom using a RNA extraction reagent, RNAWIZ™ (a product of Ambion, Inc.), following an attached protocol. From the total RNA thus obtained, mRNA was prepared, and then cDNA was synthesized by a vector-capping method (Kato, S. et al., DNA Res., 12, 53-62, 2005). Subsequently, fragments of the cDNA thus obtained were incorporated into plasmid vectors, pGCAPzf3 (Tsugane, T. et al., Plant Biotechnology., 22, 161-165, 2005), thereby a cDNA library was constructed.

Example 2

Preparation of mRNA from a Plant Belonging to the Genus *Glychyrrhiza* and Production of a cDNA Library (2)

A stolon (underground stem) of *Glychyrrhiza uralensis* presumed to have been cultivated for four years or longer after a final transplant in a field at Research Center for Medicinal Plant Resources, Tsukuba Division (Tsukuba city, Ibaraki), of National Institute of Biomedical Innovation, was harvested in October. A total RNA was prepared therefrom using a RNA extraction reagent, Trizol (a product of Invitrogen Corporation), and a purification column, RNeasy (a product of Qiagen) following attached protocols. From the total RNA thus obtained, mRNA was prepared, and then cDNA was synthesized by an oligo-capping method (Murayama, K. et al., Gene, 138, 171-174, 1994, and Suzuki, Y. et al., Gene, 200, 149-156). Subsequently, fragments of the cDNA thus obtained were incorporated into plasmid vectors, pCMVFL3, thereby a cDNA library was constructed.

Example 3

Sequence Analysis (1)

A strain of *Escherichia coli*, DH12S (a product of Invitrogen Corporation), or T1 phage resistant DH10B (a product of Invitrogen Corporation) was transformed with the cDNA library obtained in Example 1, and approximately 30,000 single colonies thus obtained were picked up in 384 plates. DNA to be used as a template in a sequencing reaction was amplified by a colony PCR, and the DNA thus amplified was purified by ethanol precipitation. Using the DNA thus purified as a template, sequencing reactions were carried out from a 5' end side of each cDNA fragment with BigDye ver 3.1, a product of Applied Biosystems. Subsequent to purification with ethanol precipitation, polynucleotide sequences were analyzed by 3730×1 DNA Analyzer (a product of Applied Biosystems).

Example 4

Sequence Analysis (2)

A strain of *Escherichia coli*, DH5α was transformed with the cDNA library obtained in Example 2, and approximately 26,000 single colonies thus obtained were picked up in 384 plates. DNA to be used as a template in a sequencing reaction was amplified by a colony PCR, and the DNA thus amplified was purified by ethanol precipitation. Using the DNA thus purified as a template, sequencing reactions were carried out from a 5' end side of each cDNA fragment with BigDye ver 3.1 (a product of Applied Biosystems). Subsequent to purification with ethanol precipitation, polynucleotide sequences of the DNA were analyzed by 3730×1 DNA Analyzer (a product of Applied Biosystems).

Example 5

Clustering of EST (Expression Sequence Tag)

Approximately 30,000 EST data obtained from RIKEN (Example 3) and approximately 26,000 EST data obtained from NEDO (New Energy and Industrial Technology Development Organization) (Example 4) were integrated into one set of data, and clustering was performed with a PHRAP program (World Wide Web.phrap.org). As a result, 10,372 unique contigs were obtained.

Example 6

Extraction of P450 Gene Through a Homology Search

A BLASTX search was conducted (Altschul, S. F. et al., Nucleic Acids Res. 25, 3389-3402, 1997) with respect to known proteins registered in a database of NCBI (National Center for Biotechnology Information) using 10,372 contig sequences obtained in Example 5 as queries, and contigs having a high homology to known P450 monooxygenase registered in the database were selected. Among a plurality of EST clones constructing the selected contigs, plasmid DNA was prepared for a clone determined to retain a longest 5' terminal region, and full-length polynucleotide sequences of each of cloned cDNA fragments (36 fragments) were determined.

Example 7

Gene Expression Analysis

In order to select a molecular species which is highly likely to be involved in biosynthesis of glycyrrhizin from among 36 P450 molecular species obtained in Example 6, it was examined in what organ in *Glychyrrhiza uralensis* each P450 molecular species was expressed by a RT-PCR method.

A total RNA was prepared from a total of four kinds of different plant tissues including an underground part where glycyrrhizin is highly accumulated (a thickened root and a stolon) and an aboveground part where glycyrrhizin is not detected at all (a leave and a stem). Using 1 µg of the total RNA thus obtained, a first-strand cDNA synthesis was conducted with a SMART RACE cDNA amplification kit (a product of Clontech Laboratories) following an attached protocol.

Sense primers and antisense primers specifically annealing to each P450 gene were designed, and PCR was conducted for 25 to 30 cycles with a Takara Ex Taq™ DNA polymerase (a product of Takara Shuzo Co., Ltd.) using four kinds of first strand DNA, each 2 µl, as templates. The PCR fragments thus obtained were analyzed by agarose gel electrophoresis (FIG. 1), and P450 molecular species with which the amplification of PCR fragments was observed only in a case when first-strand cDNA templates derived from a root and a stolon were employed were selected. Among the selected P450 molecular species, P450 molecular species (I) and (II), which were confirmed to have such an enzymatic activity as to oxidize a triterpene (corresponding to bands indicated by an arrow in an electrophoresis image in FIG. 1) are described in the following Examples.

Example 8

Amplification and Cloning of Full-Length Coding Regions of P450 Molecular Species (I) and (II)

Using the first-strand cDNA derived from a stolon of *Glychyrrhiza uralensis* prepared in Example 7 as a template, PCR reactions (30 cycles, using a Pfu-Turbo DNA Polymerase, a product of Stratagene) were carried out with an annealing temperature of 55° C., using oligo DNA (SEQ ID NOs: 5 and 6), which were sites corresponding to N-termini and C-termini of polypeptides of P450 molecular species (I) and (II), as primers. It is to be noted that four nucleotides (cacc) are attached to a 5' end of the primer of SEQ ID NO:5, which are necessary for cloning into an entry vector, pENTR™/D-TOPO (trademark) (a product of Invitrogen Corporation). DNA fragments amplified by the PCR were cloned into pENTR/D-TOPO entry vectors, and polynucleotide sequences were determined for six independent clones thus obtained. Two kinds of polynucleotide sequences thus obtained are SEQ ID NO:3 and SEQ ID NO:4, and polypeptide sequences predicted from each of them are SEQ ID NO:1 and SEQ ID NO:2, respectively. The polynucleotide shown in SEQ ID NO:3 and the polynucleotide shown in SEQ ID NO:4 differ at 11 nucleotides, namely, at positions 26, 163, 197, 294, 480, 591, 900, 945, 1089, 1373, and 1434. Also, the polypeptide shown in SEQ ID NO:1 and the polypeptide shown in SEQ ID NO:2 differ at four amino acids, namely, at positions 9, 55, 66, and 458.

Example 9

Construction of an Expression Vector for the Protein of the Present Invention Using a Baculovirus-Insect Cell Expression System Plasmids containing each of polynucleotides shown in SEQ ID NO:3 and SEQ ID NO:4 produced in Example 8 (entry clones) and a destination vector, pDEST™ 8 (a product of Invitrogen Corporation) were mixed, and DNA fragments shown in SEQ ID NO:3 and SEQ ID NO:4 were transferred to the pDEST™ 8 vector by a nucleotide sequence-specific recombination reaction (GATEWAY™ attL×attR reaction), thereby a construct for expression in an insect cell was produced. A strain of *Escherichia coli*, DH10Bac (a product of Invitrogen Corporation), was transformed with the construct thus obtained by a calcium chloride method. Bacmid DNA (a primary recombinant baculovirus) was prepared from colonies thus obtained following an attached protocol.

Example 10

Expression of the Protein of the Present Invention Using a Baculovirus-Insect Cell Expression System In accordance with an ordinary method (a product of Invitrogen Corporation, Bac-to-Bac Baculovirus Expression System, catalog number of 10359016), the Bacmid DNA produced in Example 9 was allowed to infect and replicate in insect cells (*Spodoptera frugiperda* 9), and a purified virus liquid with a high titer (the titer=approximately $1 \times 10^8$ pfu/ml) was prepared. In 3 ml of Grace's Insect Cell Culture Medium (a product of GIBCO BRL), $1.0 \times 10^6$ insect cells were suspended, to which 30 µl of the high titer virus liquid was added, and the mixture was incubated at room temperature for 30 minutes. To the mixture, 50 ml of Grace's Insect Cell Culture Medium (containing an aminolevulinic acid at a final concentration of 100 μM, a fetal bovine serum at a final concentration of 10%, a citric acid at a final concentration of 100 μM, and Pluronic F68 at a final concentration of 0.1%) was added. The mixture was then transferred to a 300 ml-flask and cultured at 27° C. for 96 hours at 150 rpm.

Example 11

Preparation of a Microsomal Fraction from the Insect Cell

The insect cell culture liquid obtained in Example 10 (50 ml) was centrifuged at 2,330 g for five minutes at 4° C. to collect the insect cells. The insect cells thus collected were washed three times with ice-cold phosphate-buffered saline and then suspended in 5 ml of 50 mM phosphate-potassium buffer (pH 7.2, containing 1 mM EDTA, 1 mM DTT, and 20% Glycerol). The cells were disrupted by sonication with BRANSON SONIFER 250 (a product of Branson Ultrasonics Corporation), followed by centrifugation at 2,330 g for 20 minutes at 4° C. A supernatant was subsequently collected and subjected to centrifugation at 100,000 g for one hour at 4° C. Pellets (microsomal fraction) thus obtained were suspended in 2 ml of 50 mM phosphate-potassium buffer (pH 7.2, containing 1 mM EDTA, 1 mM DTT, and 20% Glycerol).

Example 12

Preparation of a Triterpenoid as a Substrate

Figure 3:
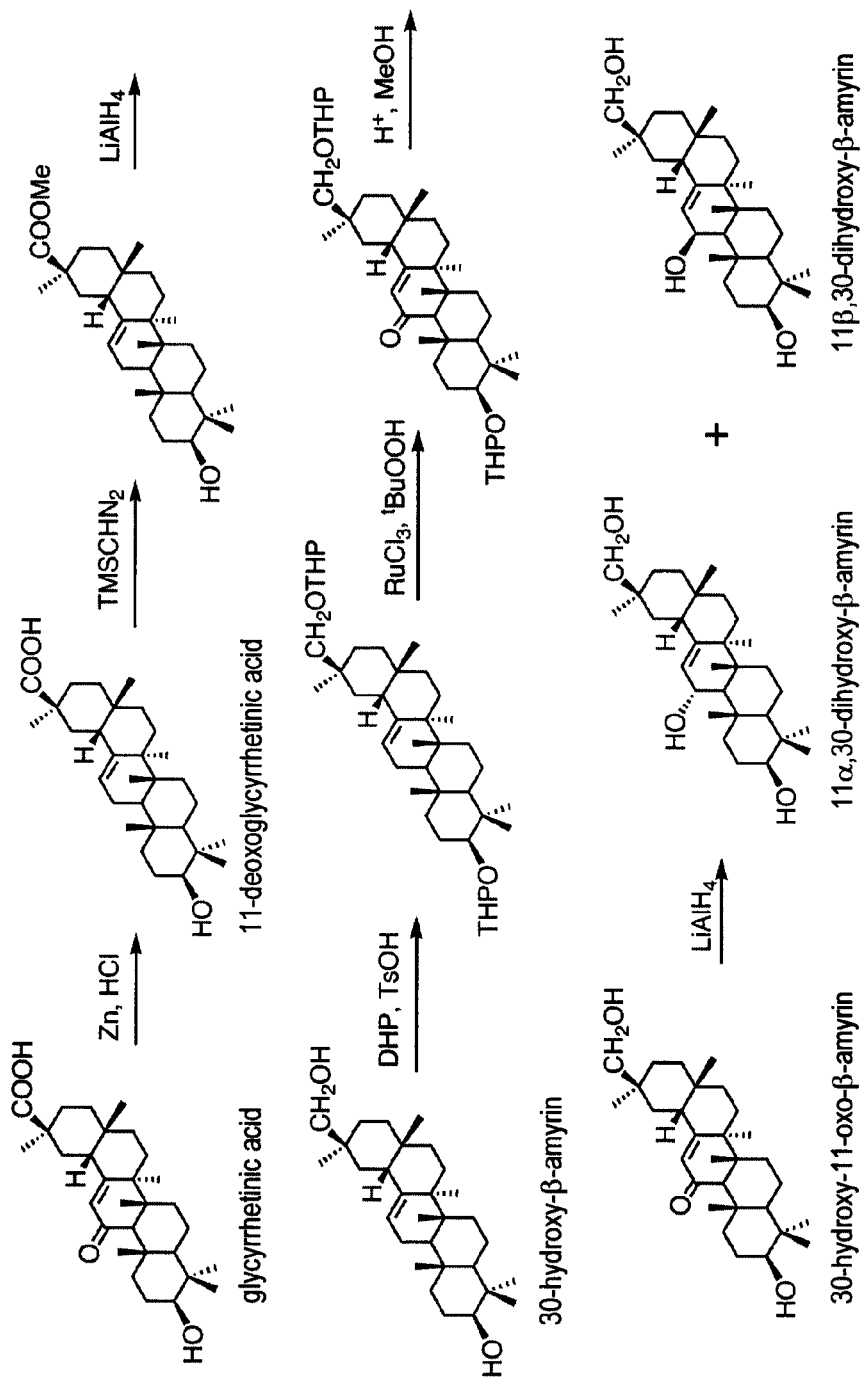
FIG. 3 shows a method for synthesizing a triterpenoid.

A triterpenoid to be used in an activation assay employing the microsomal fraction were synthesized by methods shown in FIG. 2 and FIG. 3.
1) β-amyrin
Oleanolic acid (a product of Sigma-Aldrich Corporation) was reacted on trimethylsilyldiazomethane to convert a carboxylic acid into a methyl ester and protect a hydroxyl group as a tert-butyldimethylsilyl group. The methyl ester was reduced to an alcohol, on which mesyl chloride was acted to obtain a mesyl ester, which was then converted into a methyl by a reductive substitution reaction. The methyl thus obtained was deprotected to provide β-amyrin. A structure thereof was confirmed by analyzing $^1$H-NMR and $^{13}$C-NMR spectra.
2) 11-oxo-β-amyrin
A hydroxyl group at the position 3 of β-amyrin was protected with a tetrahydropyranyl group, and ruthenium chloride and tert-butyl hydroperoxide were acted thereon to convert a methylene carbon at the position 11 into a carbonyl group. Subsequently, deprotection was conducted to provide 11-oxo-β-amyrin. A structure thereof was confirmed by analyzing $^1$H-NMR and $^{13}$C-NMR spectra.
3) 11α-hydroxy-β-amyrin
Lithium aluminium hydride was acted on 11-oxo-β-amyrin to reduce a carbonyl group at the position 11, and then the compound thus obtained was separated by silica gel column chromatography to provide 11α-hydroxy-β-amyrin and 11β-hydroxy-β-amyrin. Structures thereof were confirmed by analyzing $^1$H-NMR and $^{13}$C-NMR spectra.
4) 11-deoxoglycyrrhetinic acid
Zinc and hydrochloric acid were acted on glycyrrhetinic acid (a product of Sigma-Aldrich Corporation) to reduce a carbonyl group at the position 11 to provide 11-deoxoglycyrrhetinic acid. A structure thereof was confirmed by analyzing $^1$H-NMR and $^{13}$C-NMR spectra.
5) 30-hydroxy-β-amyrin
Trimethylsilyldiazomethane was acted on 11-deoxoglycyrrhetinic acid to convert a carboxylic acid into a methyl ester, after which the ester was reduced to provide 30-hydroxy-β-amyrin. A structure thereof was confirmed by analyzing $^1$H-NMR and $^{13}$C-NMR spectra.
6) 30-hydroxy-11-oxo-β-amyrin
A hydroxyl group of 30-hydroxy-β-amyrin was protected as a tetrahydropyranyl group, and ruthenium chloride and tert-butyl hydroperoxide were acted thereon to convert a methylene carbon at the position 11 into a carbonyl group. Subsequently, deprotection was conducted to provide 30-hydroxy-11-oxo-β-amyrin. A structure thereof was confirmed by analyzing $^1$H-NMR and $^{13}$C-NMR spectra.
7) 11α,30-dihydroxy-β-amyrin
Lithium aluminium hydride was acted on 30-hydroxy-11-oxo-β-amyrin to reduce a carbonyl group at the position 11, and then the compound thus obtained was separated by silica gel column chromatography to provide 11α,30-dihydroxy-β-amyrin and 11β,30-dihydroxy-β-amyrin. Structures thereof were confirmed by analyzing $^1$H-NMR and $^{13}$C-NMR spectra.

Example 13

In Vitro Assay Using the Microsomal Fraction

After mixing 50 μl of the microsomal fraction obtained in Example 11, 25 μl of 1M phosphate-potassium buffer (pH 7.2), 1 μl (a final concentration of 0.1 unit/rill) of purified *Arabidopsis* P450 reductase (Mizutani, M. and Ohta, D., Plant Physiol. 116, 357-367, 1998), 25 μl (a final concentration of 1 mM) of NADPH, 5 μl (a final concentration of 20 μM) of reaction substrate (β-amyrin or 30-hydroxy-β-amyrin), and 394 μl of sterilized water, the mixture thus obtained was incubated for two hours while stirring at 30° C. at 1,000 rpm.

Example 14

Identification of a Converted Product

The reaction solution obtained in Example 13 was extracted on ethyl acetate, after which a solvent was removed by drying from the ethyl acetate part. Subsequently, N-methyl-N-(trimethylsilyl)trifluoroacetamide was added thereto and the mixture was heated at 80° C. for 30 minutes for derivatization of products into a trimethylsilyl ether, thereby a sample for a GC-MS analysis was provided. Automass (JEOL)-6890N (a product of Agilent technologies) was used for GC-MS, and HP-5 column (a product of J&W Scientific Inc.; 0.32 mm×30 m; 0.25 mm film thickness) was used for a column to analyze converted products. Identification of converted products was determined by comparing retention time of GC and MS spectra using the triterpenoid prepared in Example 12 as an authentic sample.

Figure 4:
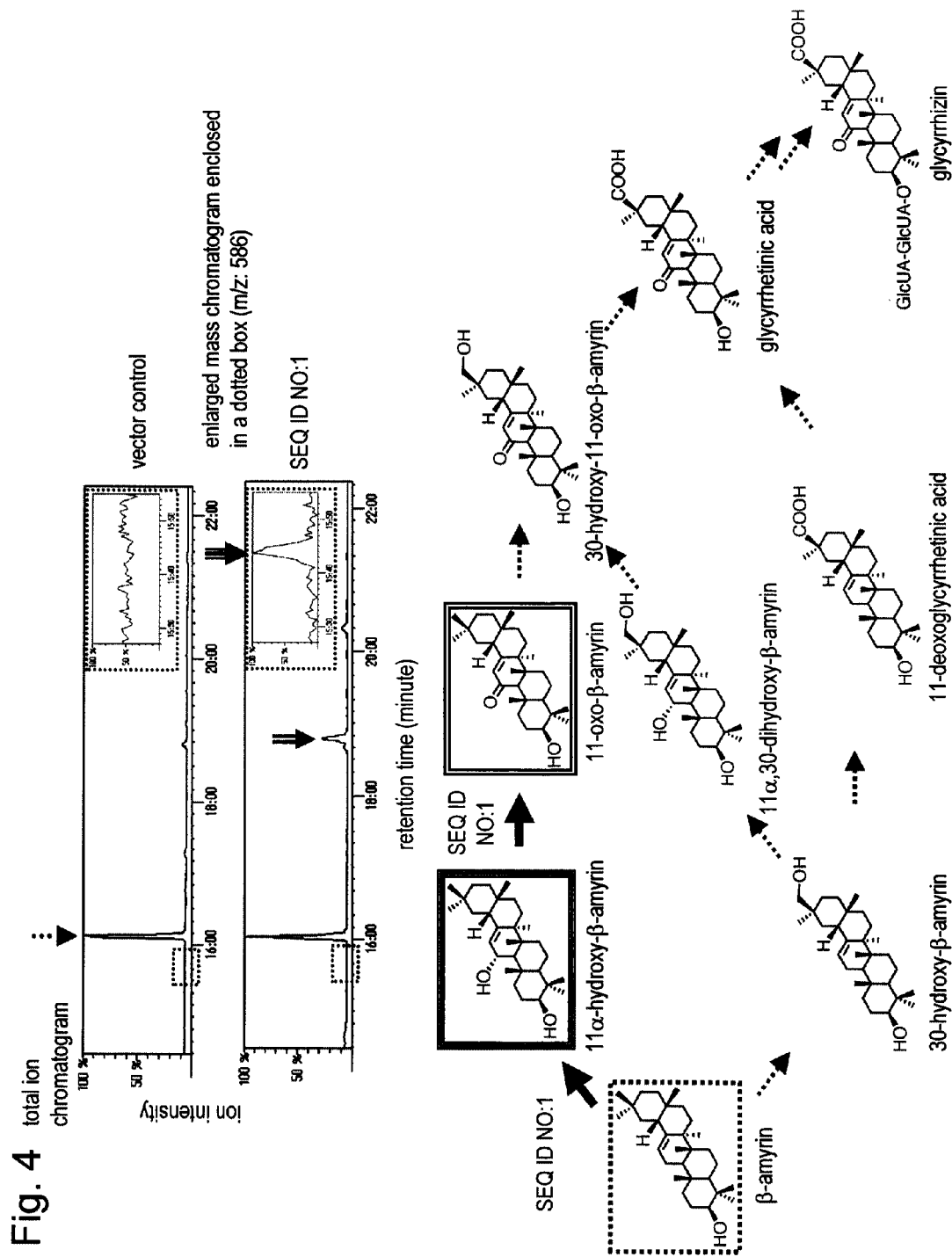
FIG. 4 shows results of detection of a converted product of β-amyrin by the protein of the present invention.
Figure 5:
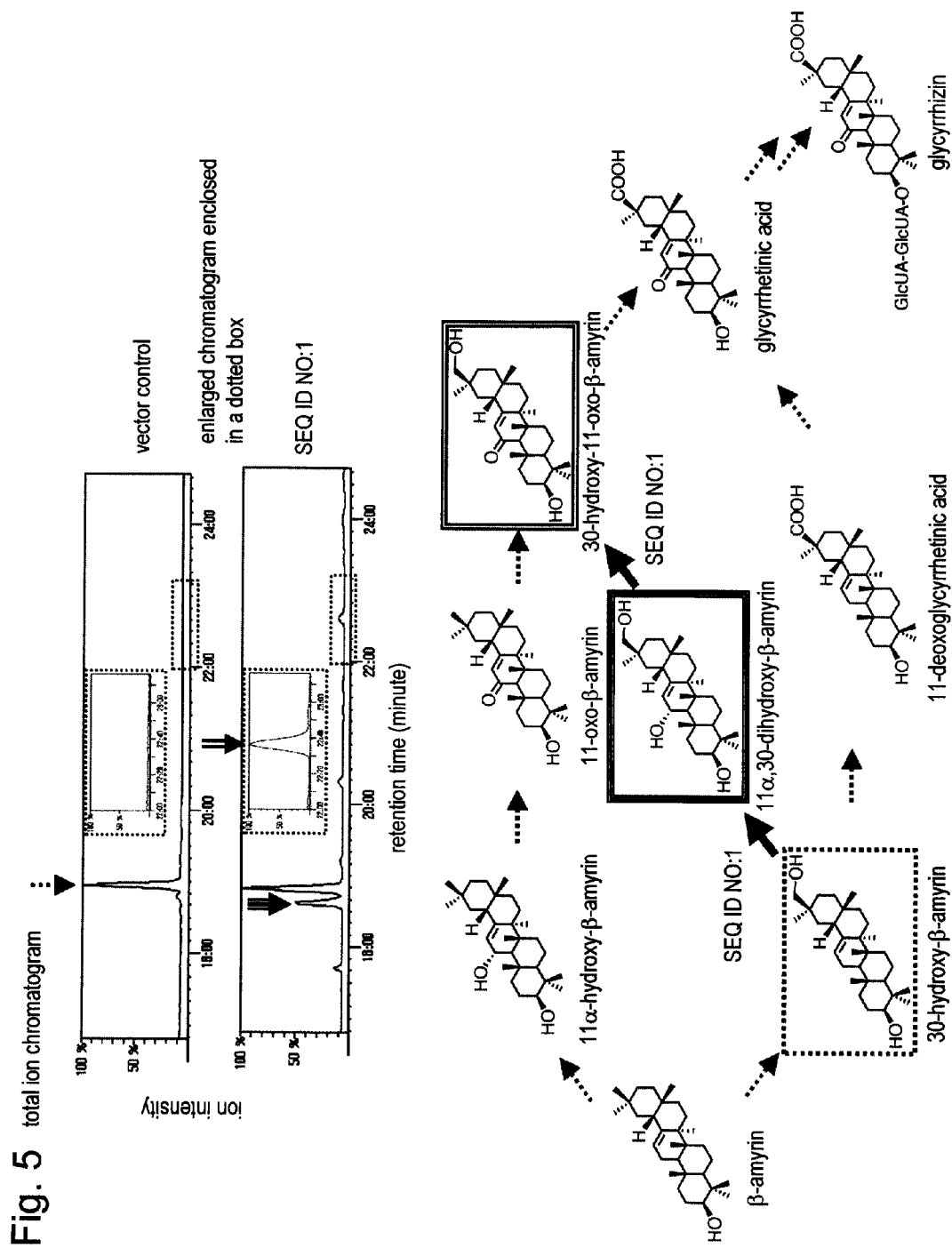
FIG. 5 shows results of detection of a converted product of 30-hydroxy-β-amyrin by the protein of the present invention.

As a result of enzymatic assays using the microsomes prepared from each of an insect cell expressing the polypeptide shown in SEQ ID NO:1 and an insect cell expressing the polypeptide shown in SEQ ID NO:2, 11α-hydroxy-β-amyrin and 11-oxo-β-amyrin were detected as converted products of β-amyrin in either of the above cases. FIG. 4 shows results obtained by using the polypeptide of SEQ ID NO:1. A dotted-line arrow indicates β-amyrin, a double-line arrow indicates 11-oxo-β-amyrin, and a triple-line arrow indicates 11α-hydroxy-β-amyrin in a total ion chromatogram. When the polypeptide of SEQ ID NO:2 was used, results similar to the case in which the polypeptide of SEQ ID NO:1 was used were obtained. Further, when 30-hydroxy-β-amyrin and the polypeptide of SEQ ID NO:1 were reacted, 11α,30-dihydroxy-β-amyrin and 30-hydroxy-11-oxo-β-amyrin were detected. FIG. 5 shows results obtained by using the polypeptide of SEQ ID NO: 1. A dotted-line arrow indicates 30-hydroxy-β-amyrin, a double-line arrow indicates 30-hydroxy-11-oxo-β-amyrin, and a triple-line arrow indicates 11α,30-dihydroxy-β-amyrin in a total ion chromatogram. When the polypeptide of SEQ ID NO:2 was used, results similar to the case in which the polypeptide of SEQ ID NO:1 was used were obtained. On the other hand, as a control experiment, a similar experiment was performed using a microsomal fraction derived from an insect cell in which a void vector was introduced. When β-amyrin was used as a reaction substrate, neither 11α-hydroxy-β-amyrin nor 11-oxo-β-amyrin was produced as shown in a total ion chromatogram for a vector control in FIG. 4. When 30-hydroxy-β-amyrin was used as a reaction substrate, neither 11α,30-dihydroxy-β-amyrin nor 30-hydroxy-11-oxo-β-amyrin was produced as shown in a total ion chromatogram for a vector control in FIG. 5. As shown above, a triterpene enzyme presumed to be involved in a biosynthesis of glycyrrhizin which oxidizes the position 11 of a β-amyrin skeleton and converts the same into a hydroxyl group and a carbonyl group was identified for the first time.

Example 15

Construction of pESC-LEU-LjCPR, a Yeast Expression Vector for *Lotus* P450 Reductase Searching through a *Lotus* EST database (provided by Kazusa DNA Research Institute), sequences having 70% or more identity with *Arabidopsis* P450 reductase at an amino acid level were selected. EST clones which presumably contained a full-length coding region (accession no. AV778635) were obtained from Kazusa DNA Research Institute, and DNA sequences were determined with ABI PRISM 3100 Genetic Analyzer (hereinafter called LjCPR). Using LjCPR-introduced plasmids (pBluescript SK (−)) as templates, and using primers of both of CPR-F (Not), GGGCGGCCGCAC-TAGTATCGATGGAAGAATCAAGCTCCATGAAG (SEQ ID NO:7) and CPR-R (Pac), TTAATTAATCACCATACAT-CACGCAAATAC (SEQ ID NO:8), PCR reactions were carried out for 15 cycles with KOD-Plus- (a product of Toyobo, Co., Ltd.), where one cycle included; 94° C. for two minutes, followed by 94° C. for 20 seconds, 60° C. for 40 seconds, and keeping samples at 68° C. for two minutes. The samples were further kept at 68° C. for two minutes. The PCR reaction products thus obtained were ligated with pT7Blue T-vectors (a product of Novagen) using TAget Clone-Plus- (a product of Toyobo, Co., Ltd.) After confirming DNA sequences thereof, the ligated vectors thus obtained were digested with NotI and PacI, while yeast expression vectors, pESC-LEU (a product of Stratagene) were as well digested with NotI and PacI. Thereafter, ligation was carried out using a DNA ligation Kit Ver. 2.1 (a product of Takara Bio Inc.) to provide yeast expression vectors for LjCPR, pESC-LEU-LjCPR.

Example 16

Construction of pYES3-ADH-OSC1, a Yeast Expression Vector for cDNA of *Lotus* β-amyrin Synthase (OSC1) Gene Plasmids in which cDNA of *Lotus* β-amyrin synthase (OSC1) gene was incorporated (Sawai et al. (2006) Plant Sci 170: 247-257) were digested with KpnI and XbaI and OSC1 cDNA regions were cleaved out. Similarly, pAUR123 (a product of Takara Bio Inc.) was digested with KpnI and XbaI.

Ligation was then performed using a DNA ligation Kit Ver. 2.1 (a product of Takara Bio Inc.), thereby pAUR123-OSC1 was obtained. Using primers of both of AUR123-F, GGAT-GATCCACTAGTGGATCCTCTAGCTC-CCTAACATGTAGGTGG (SEQ ID NO:9) and AUR123-R, TAATGCAGGGCCGCAGGATCCGTGTG-GAAGAACGATTACAACAGG (SEQ ID NO:10), PCR reactions were carried out on a region from PADH1 to TADH1 in pAUR123-OSC1 for 20 cycles with KOD-Plus- (a product of Toyobo, Co., Ltd.), where one cycle included; 94° C. for two minutes, followed by 94° C. for 20 seconds, 55° C. for 40 seconds, and keeping samples at 68° C. for one and a half minutes. The samples were further kept at 68° C. for two minutes. Furthermore, using YES3-F, TGCGGCCCTGCAT-TAATGAATCGGCCAACG (SEQ ID NO:11), and YES3-R, ACTAGTGGATCATCCCCACGCGCCCTGTAG (SEQ ID NO:12), PCR reactions were carried out on a region in pYES3/CT (a product of Invitrogen Corporation) excluding from a nucleotide at position 1 to a nucleotide at position 960 (from PGAL1 to CYC1TT) for 20 cycles with KOD-Plus- (a product of Toyobo, Co., Ltd.), where one cycle included; 94° C. for two minutes, followed by 94° C. for 20 seconds, 55° C. for 40 seconds, and keeping samples at 68° C. for one and a half minutes. The samples were further kept at 68° C. for two minutes. Both of the PCR products thus obtained were linked using an In-Fusion Dry-Down PCR Cloning Kit (a product of Clontech Laboratories) to provide pYES3-ADH-OSC1, yeast expression vectors for Lotus OSC1 gene.

Example 17

Construction of a Yeast Expression Vector

A Plasmids (an entry clone) containing the polynucleotide shown in SEQ ID NO:3 produced in Example 8 and a destination vector, pYES-DEST™ 52 (a product of Invitrogen Corporation), were mixed, and DNA fragment shown in SEQ ID NO:3 was transferred to the pYES-DEST™ 52 vector by a nucleotide sequence-specific recombination reaction (GATEWAY™ attLxattR reaction), thereby a construct for expression in an yeast cell was produced.

The gene shown in SEQ ID NO:3 which had been cloned into pENTER-D-TOPO was incorporated into the yeast expression vectors, pYES-DEST52 (a product of Invitrogen Corporation), using Gateway LR Clonase IIEnzyme Mix (a product of Invitrogen Corporation), thereby a yeast expression vector for the gene shown in SEQ ID NO:3, pDEST52-GuCYP88, was provided.

Example 18

Culture of a Transformed Yeast

A yeast strain, BJ2168 (a product of Nippon Gene, Co., Ltd) (MATa prc1-407 prb1-1122 pep4-3 leu2 trp1 ura3-52 gal2) was transformed with pYES3-ADH-OSC1, pESC-LEU-LjCPR, pDEST52-GuCYP88, and pYES2 (a product of Invitrogen Corporation.) using Frozen-EZ Yeast Transformation II (a product of Zymo Research Corporation).

Example 19

Confirmation of a Product in a Transformed Yeast

Yeasts containing all three vectors of pYES3-ADH-OSC1, pESC-LEU-LjCPR, and pDEST52-GuCYP88 prepared in Example 18 were cultured in 100 ml of SC-Trp/Leu/Ura medium at 28° C. for two days at 135 rpm. The yeasts thus cultured were collected by centrifugation at 3000 g for 10 minutes and suspended in 100 ml of SC-Trp/Leu/Ura-glucose medium containing galactose (20 mg/ml) and hemin chloride (13 µg/ml), and then cultured at 28° C. for two days at 135 rpm. The yeasts were then collected by centrifugation and lyophilized. Then, 5 ml of ethyl acetate was added and both were mixed and an ethyl acetate extract was collected. After repeating the above procedure three times, the ethyl acetate extract was concentrated under reduced pressure. Yeasts containing all three vectors of pYES3-ADH-OSC1, pESC-LEU-LjCPR, and pYES2 were similarly cultured and subjected to extraction. Similarly to the method described in Example 14, a solvent was removed by drying from the ethyl acetate part, and subsequently, N-methyl-N-(trimethylsilyl)trifluoroacetamide was added thereto and the mixture was heated at 80° C. for 30 minutes for derivatization of products into a trimethylsilyl ether, thereby a sample for a GC-MS analysis was provided. Identification of converted products was determined by comparing retention time of GC and MS spectra using the triterpenoid prepared in Example 12 as an authentic sample. β-amyrin, 11α-hydroxy-β-amyrin, and 11-oxo-β-amyrin were detected from extracts of the yeasts containing all three vectors of pYES3-ADH-OSC1, pESC-LEU-LjCPR, and pDEST52-GuCYP88. On the other hand, in a control experiment conducted with yeasts containing all three vectors of pYES3-ADH-OSC1, pESC-LEU-LjCPR, and pYES2, only β-amyrin was detected, whereas neither 11α-hydroxy-β-amyrin nor 11-oxo-β-amyrin was detected from extracts of the yeasts. As shown above, it was revealed that a polypeptide encoded by the gene of the present invention was a triterpene oxidase which oxidized the position 11 of β-amyrin and converted the same into a hydroxyl group and a carbonyl group in a yeast as well.

Example 20

Identification of 11-oxo-β-amyrin by NMR

Figure 6:
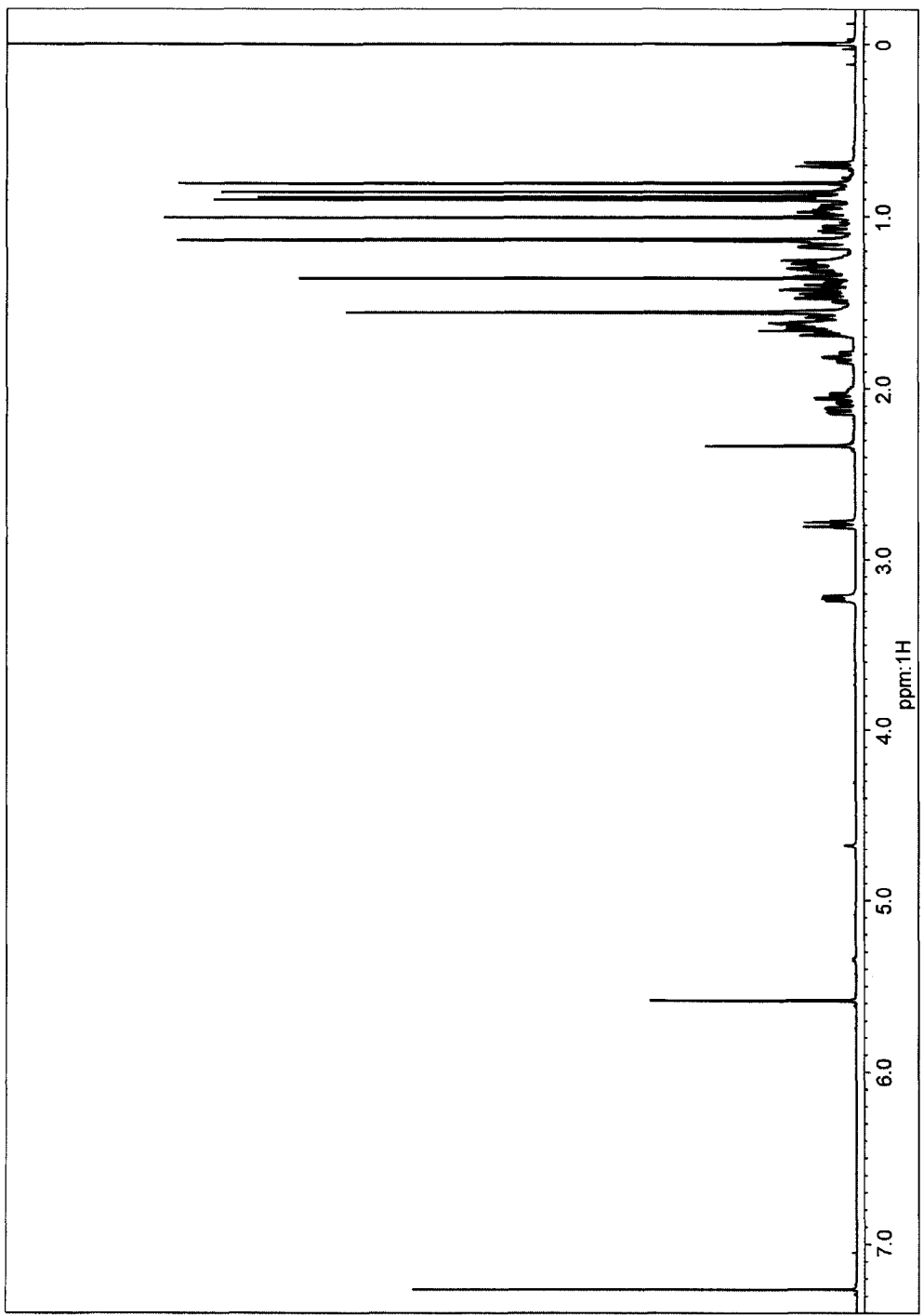
FIG. 6 shows results of measurement of 11-oxo-β-amyrin by NMR.

Yeasts containing all three vectors of pYES3-ADH-OSC1, pESC-LEU-LjCPR, and pDEST52-GuCYP88 prepared in Example 18 were cultured in 400 ml of SC-Trp/Leu/Ura medium (six containers, a total of 2.4 L) at 28° C. for two days at 125 rpm. The yeasts thus cultured were collected by centrifugation at 3000 g for 10 minutes and suspended in 400 ml of SC-Trp/Leu/Ura-glucose medium containing galactose (20 mg/ml) and hemin chloride (13 µg/ml) (six containers, a total of 2.4 L), and then cultured at 28° C. for two days at 125 rpm. The yeasts were then collected by centrifugation and lyophilized. Then, 100 ml of chloroform was added to the yeasts thus lyophilized and both were mixed, after which a chloroform extract was collected. After repeating the above procedure three times, the chloroform extract was concentrated under reduced pressure. The extract was then fractionated by silica gel chromatography. Wako gel C-300 (a product of Wako Pure Chemical Industries, Ltd.) of 2.8×40 cm in size was used as a silica gel. A solvent containing hexane:ethyl acetate at 1:1 was flowed through, and an eluate was fractionated into 7 ml-fractions. Fractions 22 to 29 were gathered and the solvent was removed, after which the gathered fractions were subjected to a silica gel TLC plate LK6F (a product of Whatman) of 20×20 cm. After the plate was developed with a solvent having toluene:acetone at 19:1, a silica gel exhibiting a same Rf value as 11-oxo-β-amyrin was scratched off and eluted in chloroform. After removing the solvent, a remaining substance was dissolved in deuterated chloroform and $^1$H-NMR spectrum was measured by a NMR (500 MHz) manufactured by Japan Electron Optics Laboratory. As a result, $^1$H-NMR spectrum of the above two fractions was perfectly coincided with $^1$H-NMR spectrum of 11-oxo-β-amyrin, which was an authentic product prepared in Example 12. (CDCl$_3$, 500 MHz: δ 0.81 (3H, s), 0.86 (3H, s), 0.89 (3H, s), 0.90 (3H, s), 1.00 (3H, s), 1.13 (3H, s), 1.14 (3H, s), 1.36 (3H, s) 2.34 (1H, s), 2.79 (1H, dt, J=3.4, 13.8 Hz), 3.23 (1H, dd, J=5.2, 10.9 Hz), 5.59 (1H, s)) The $^1$H-NMR spectrum was shown in FIG. 6.

Example 21

Identification of 11α-hydroxy-β-amyrin by NMR

Figure 7:
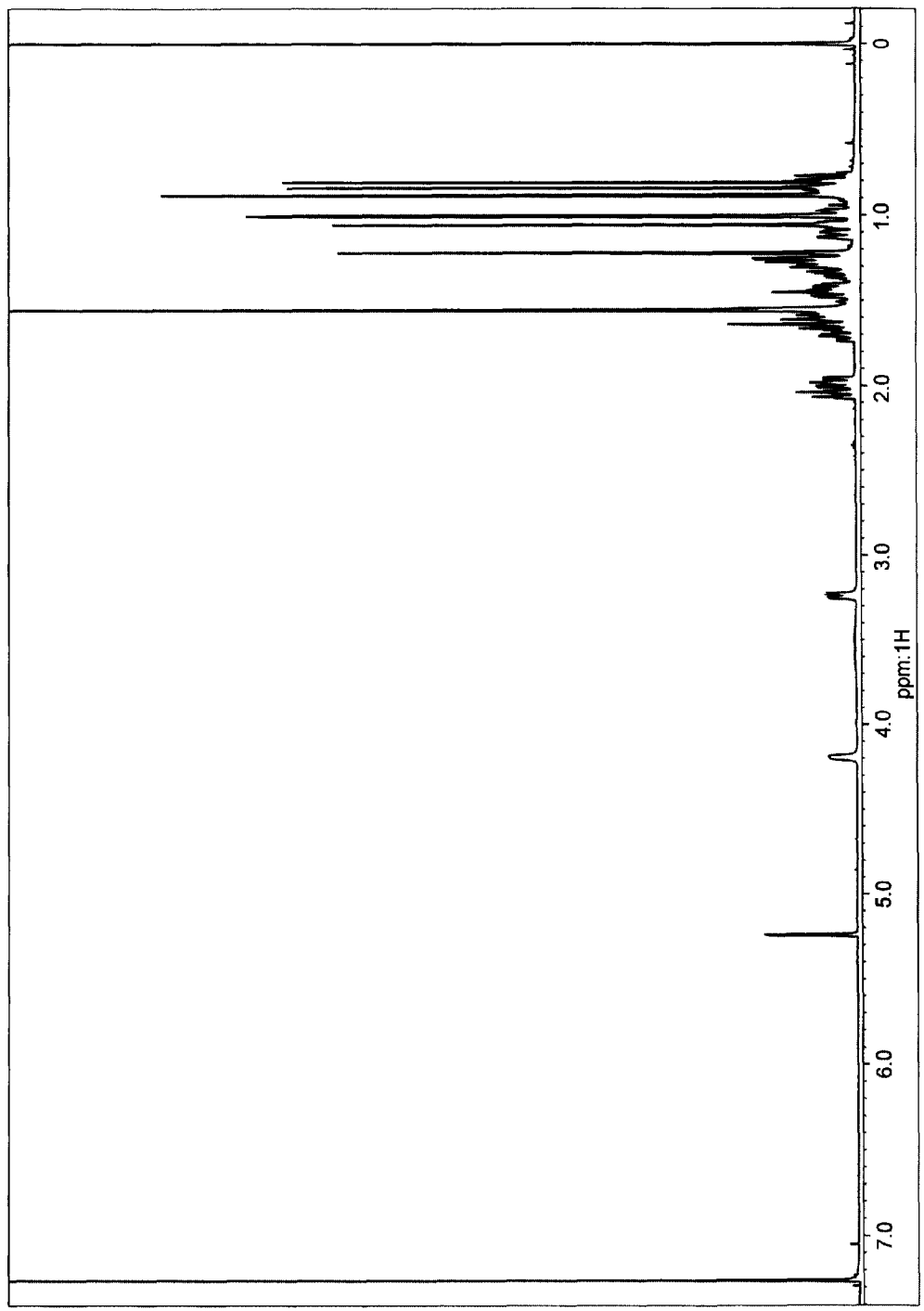
FIG. 7 shows results of measurement of 11α-hydroxy-β-amyrin by NMR.

Yeasts containing all three vectors of pYES3-ADH-OSC1, pESC-LEU-LjCPR, and pDEST52-GuCYP88 prepared in Example 18 were cultured in 400 ml of SC-Trp/Leu/Ura medium (12 containers, a total of 4.8 L) at 28° C. for two days at 125 rpm. The yeasts thus cultured were collected by centrifugation at 3000 g for 10 minutes and suspended in 400 ml of SC-Trp/Leu/Ura-glucose medium containing galactose (20 mg/ml) and hemin chloride (13 µg/ml) (12 containers, a total of 4.8 L), and then cultured at 28° C. for two days at 125 rpm. The yeasts were then collected by centrifugation and lyophilized. Then, 100 ml of ethyl acetate was added to the yeasts thus lyophilized and both were mixed, after which an ethyl acetate extract was collected. After repeating the above procedure three times, the ethyl acetate extract was concentrated under reduced pressure. The extract was then fractionated by silica gel chromatography. Wako gel C-200 (a product of Wako Pure Chemical Industries, Ltd.) of 2.8×40 cm in size was used as a silica gel. A solvent containing hexane:ethyl acetate at 1:1 was flowed through, and an eluate was fractionated into 7 ml-fractions. Fractions 43 to 57 were taken together to remove the solvent, after which the residue was subjected to a silica gel TLC plate LK6F (a product of Whatman) of 20×20 cm. After the plate was developed with a solvent having hexane:ethyl acetate at 1:1, a silica gel exhibiting a same Rf value as 11α-hydroxy-β-amyrin was scratched off and eluted in chloroform. After removing the solvent, a remaining substance was dissolved in deuterated chloroform and $^1$H-NMR spectrum was measured by a NMR (500 MHz) manufactured by Japan Electron Optics Laboratory. As a result, $^1$H-NMR spectrum of the above fraction was perfectly coincided with $^1$H-NMR spectrum of 11α-hydroxy-β-amyrin, which was an authentic product prepared in Example YY. (CDCl$_3$, 500 MHz: δ 0.81 (3H, s), 0.84 (3H, s), 0.89 (6H, s), 1.00 (3H, s), 1.01 (3H, s), 1.06 (3H, s), 1.22 (3H, s), 3.24 (1H, dd, J=4.9, 11.2 Hz), 4.19 (1H, m), 5.24 (1H, d, J=4.0 Hz)). The $^1$H-NMR spectrum was shown in FIG. 7.

Example 22

Construction of a Plant Expression Vector

Entry clones having the polynucleotide shown in SEQ ID NO:3 were mixed with binary vectors for plant transformation, pBI-OX-GW (a product of Inplanta Innovations, Inc.) or pHR-OX (gfp) (SEKI and MURANAKA, Bioscience & Bioindustry, 64, 17-22, 2006), and DNA fragments shown in SEQ ID NO:3 were incorporated into pBI-OX-GW and pHR-OX (gfp) through a nucleotide sequence-specific recombination reaction (GATEWAY™ attL×attR reaction).

Example 23

Transformation of Arabidopsis

Each plant transformation construct obtained in Example 22 was introduced into an *Agrobacterium tumefaciens*

GV3101 (pMP90) strain. Using *Agrobacterium tumefaciens* having each plant transformation construct, transformed seeds of *Arabidopsis* (ecotype Col-0) were obtained by a known method (Clough, S. J. and Bent, A. F., Plant J., 16, 735-743, 1998). After disinfecting surfaces of the transformed seeds thus obtained with ethanol, they were seeded in MS agar medium containing 50 mg/l of kanamycin and 250 mg/l of Claforan (a product of Aventis Pharma Ltd.) and cultured at 23° C. for 16 hours in day length, thereby transformed *Arabidopsis* having the polynucleotide shown in SEQ ID NO:3 was selected. Individual *Arabidopsis* plants highly expressing the polypeptide shown in SEQ ID NO:1 can be obtained by transformation using pBI-OX-GW (a product of Inplanta Innovations, Inc.) Also, from individual plants transformed with pHR-OX (gfp) vectors having rol gene clusters (a set of genes needed for induction of a hairy root) derived from *Agrobacterium rhizogenes* on T-DNA, hairy root culture of *Arabidopsis* highly expressing the polypeptide shown in SEQ ID NO:1 can be produced, which can be then maintained by culture for a long term by a known method (Seki, H. et al., Plant Mol. Biol., 59, 793-807, 2005).

Example 24

Isolation of a Triterpene Oxidase Gene from *Glychyrrhiza glabra*

*Glychyrrhiza glabra*, which is one of plants belonging to the genus *Glychyrrhiza*, produces glycyrrhizin similarly to *Glychyrrhiza uralensis*. A homologous gene presumed to have a function equivalent to the genes shown in SEQ ID NOs: 3 and 4 was isolated from *Glychyrrhiza glabra* by a RT-PCR method.

In a similar manner to Example 8, cDNA was isolated from stolons of *Glychyrrhiza glabra* provided by Research Center for Medicinal Plant Resources, Hokkaido Division, of National Institute of Biomedical Innovation (Nayoro city, Hokkaido). Polynucleotide sequences of independent six clones thus obtained were determined. The sequence thus obtained is SEQ ID NO:14, and a polypeptide sequence predicted therefrom is SEQ ID NO:13. The SEQ ID NO:13 had a 98.6% identity with the amino acid sequences shown in SEQ ID NO:1 and SEQ ID NO:2.

Further, as a result of the examination of a β-amyrin oxidation activity of the polypeptide shown in SEQ ID NO:13 in the transformed yeasts in accordance with the methods shown in Examples 13 to 17, it was found that the polypeptide shown in SEQ ID NO:13 was a triterpene oxidase which oxidized the position 11 of β-amyrin and converted the same into a hydroxyl group and a carbonyl group similarly to the polypeptides shown in SEQ ID NO:1 and SEQ ID NO:2, which were obtained from *Glychyrrhiza uralensis*.

INDUSTRIAL APPLICABILITY

According to the present invention, a protein which oxidizes a carbon at the position 11 of a dammarane-type triterpene and a gene encoding the same can be provided, and for example, the protein can be applied to synthesis of glycyrrhizin, or a production amount of glycyrrhizin can be increased by introducing the aforementioned gene into a plant belonging to the genus *Glychyrrhiza* and the like and expressing the gene at a high level.

The present invention can be applied to elucidation of the biosynthetic pathway of glycyrrhizin from β-amyrin. Also, The present invention can increase an amount of glycyrrhizin produced by a plant belonging to the genus *Glychyrrhiza*. Furthermore, the present invention can be applied to an industrial production of glycyrrhizin.

All of publications, patents and patent applications cited herein are incorporated herein by reference in their entirety.

The invention claimed is:

1. An isolated nucleic acid comprising a nucleotide sequence selected from the group consisting of:
    (a) the nucleotide sequence comprising SEQ ID NO: 3; and
    (b) a nucleotide sequence having 95% or more identity with the nucleotide sequence of SEQ ID NO: 3.

2. The isolated nucleic acid of claim 1, derived from a plant belonging to a genus *Glychyrrhiza*.

3. The isolated nucleic acid of claim 2, wherein the plant belonging to the genus *Glychyrrhiza* is *Glychyrrhiza uralensis* or *Glychyrrhiza glabra*.

4. The isolated nucleic acid according to claim 1, comprising the nucleotide sequence shown in SEQ ID NO:4 or SEQ ID NO:14.

5. A recombinant vector comprising the isolated nucleic acid of claim 1.

6. A bacterial, insect cell, fungi, or plant transformant comprising the isolated nucleic acid of claim 1.

7. The transformant of claim 6, in the form of a plant belonging to the genus *Glychyrrhiza*.

8. The transformant of claim 7, wherein the plant belonging to the genus *Glychyrrhiza* is *Glychyrrhiza uralensis* or *Glychyrrhiza glabra*.

9. The transformant of claim 6, wherein expression of the nucleic acid is enhanced.

10. A method for producing an isolated protein, the method comprising culturing or growing a transformant which is transformed with a nucleic acid that encodes the protein having the amino acid sequence of SEQ ID NOs: 1, 2, or 13, or a recombinant vector comprising a nucleic acid encoding the protein having the amino acid sequence of SEQ ID NOs: 1, 2, or 13, thereby obtaining a culture or growth product, and collecting the protein from the obtained culture or growth product,
    wherein the transformant is a bacterial, insect cell, fungi, or plant transformant, and
    wherein the isolated protein comprises an amino acid sequence selected from the group consisting of:
    (a) the amino acid sequence comprising SEQ ID NO: 1; and
    (b) an amino acid sequence having 95% or more identity with the amino acid sequence of SEQ ID NO: 1.

11. A method for oxidizing a triterpene compound produced from a dammarane cation, in which 2,3-oxidosqualene is cyclized in a chair-chair-chair-boat conformation, the method comprising acting an isolated protein on the triterpene compound,
    wherein the isolated protein comprises an amino acid sequence selected from the group consisting of:
    (a) the amino acid sequence comprising SEQ ID NO: 1; and
    (b) an amino acid sequence having 95% or more identity with the amino acid sequence of SEQ ID NO: 1.

12. A method for selecting a plant by determining the presence or absence, or an expression level, of the nucleic acid of claim 1 in a plant, the method comprising detecting the nucleic acid or quantitating the nucleic acid expression level by conducting PCR, RT-PCR, or nucleic acid hybridization with the nucleic acid or a fragment of the nucleic acid in a sample comprising a nucleic acid prepared from the plant, and selecting the plant based on the presence, absence, or expression level of the nucleic acid.

13. A bacterial, insect cell, fungi, or plant transformant comprising a recombinant vector comprising the isolated nucleic acid of claim 1.

14. The isolated nucleic acid according to claim 1, encoding a protein having an activity of oxidizing a carbon at position 11 of a triterpene compound produced from a dammarane cation, in which 2,3-oxidosqualene is cyclized in a chair-chair-chair-boat conformation.

* * * * *

SEQUENCE LISTING

```
<160> NUMBER OF SEQ ID NOS: 14

<210> SEQ ID NO 1
<211> LENGTH: 493
<212> TYPE: PRT
<213> ORGANISM: Glycyrrhiza uralensis

<400> SEQUENCE: 1

Met Glu Val His Trp Val Cys Met Ser Ala Ala Thr Leu Leu Val Cys
1               5                   10                  15

Tyr Ile Phe Gly Ser Lys Phe Val Arg Asn Leu Asn Gly Trp Tyr Tyr
                20                  25                  30

Asp Val Lys Leu Arg Arg Lys Glu His Pro Leu Pro Pro Gly Asp Met
            35                  40                  45

Gly Trp Pro Leu Ile Gly Asp Leu Leu Ser Phe Ile Lys Asp Phe Ser
        50                  55                  60

Ser Gly His Pro Asp Ser Phe Ile Asn Asn Leu Val Leu Lys Tyr Gly
65                  70                  75                  80

Arg Ser Gly Ile Tyr Lys Thr His Leu Phe Gly Asn Pro Ser Ile Ile
                85                  90                  95

Val Cys Glu Pro Gln Met Cys Arg Arg Val Leu Thr Asp Asp Val Asn
                100                 105                 110

Phe Lys Leu Gly Tyr Pro Lys Ser Ile Lys Glu Leu Ala Arg Cys Arg
            115                 120                 125
```

```
Pro Met Ile Asp Val Ser Asn Ala Glu His Arg Leu Phe Arg Arg Leu
            130                 135                 140

Ile Thr Ser Pro Ile Val Gly His Lys Ala Leu Ala Met Tyr Leu Glu
145                 150                 155                 160

Arg Leu Glu Glu Ile Val Ile Asn Ser Leu Glu Glu Leu Ser Ser Met
                    165                 170                 175

Lys His Pro Val Glu Leu Leu Lys Glu Met Lys Lys Val Ser Phe Lys
            180                 185                 190

Ala Ile Val His Val Phe Met Gly Ser Ser Asn Gln Asp Ile Ile Lys
            195                 200                 205

Lys Ile Gly Ser Ser Phe Thr Asp Leu Tyr Asn Gly Met Phe Ser Ile
210                 215                 220

Pro Ile Asn Val Pro Gly Phe Thr Phe His Lys Ala Leu Glu Ala Arg
225                 230                 235                 240

Lys Lys Leu Ala Lys Ile Val Gln Pro Val Asp Glu Arg Arg Leu
                    245                 250                 255

Met Ile Glu Asn Gly Pro Gln Glu Gly Ser Gln Arg Lys Asp Leu Ile
                260                 265                 270

Asp Ile Leu Leu Glu Val Lys Asp Glu Asn Gly Arg Lys Leu Glu Asp
            275                 280                 285

Glu Asp Ile Ser Asp Leu Leu Ile Gly Leu Leu Phe Ala Gly His Glu
290                 295                 300

Ser Thr Ala Thr Ser Leu Met Trp Ser Ile Thr Tyr Leu Thr Gln His
305                 310                 315                 320

Pro His Ile Leu Lys Lys Ala Lys Glu Glu Gln Glu Glu Ile Thr Arg
                325                 330                 335

Thr Arg Phe Ser Ser Gln Lys Gln Leu Ser Leu Lys Glu Ile Lys Gln
                340                 345                 350

Met Val Tyr Leu Ser Gln Val Ile Asp Glu Thr Leu Arg Cys Ala Asn
            355                 360                 365

Ile Ala Phe Ala Thr Phe Arg Glu Ala Thr Ala Asp Val Asn Ile Asn
            370                 375                 380

Gly Tyr Ile Ile Pro Lys Gly Trp Arg Val Leu Ile Trp Ala Arg Ala
385                 390                 395                 400

Ile His Met Asp Ser Glu Tyr Tyr Pro Asn Pro Glu Glu Phe Asn Pro
                405                 410                 415

Ser Arg Trp Asp Asp Tyr Asn Ala Lys Ala Gly Thr Phe Leu Pro Phe
                420                 425                 430

Gly Ala Gly Ser Arg Leu Cys Pro Gly Ala Asp Leu Ala Lys Leu Glu
            435                 440                 445

Ile Ser Ile Phe Leu His Tyr Phe Leu Arg Asn Tyr Arg Leu Glu Arg
450                 455                 460

Ile Asn Pro Glu Cys His Val Thr Ser Leu Pro Val Ser Lys Pro Thr
465                 470                 475                 480

Asp Asn Cys Leu Ala Lys Val Ile Lys Val Ser Cys Ala
                485                 490

<210> SEQ ID NO 2
<211> LENGTH: 493
<212> TYPE: PRT
<213> ORGANISM: Glycyrrhiza uralensis

<400> SEQUENCE: 2

Met Glu Val His Trp Val Cys Met Cys Ala Ala Thr Leu Leu Val Cys
1               5                   10                  15
```

```
Tyr Ile Phe Gly Ser Lys Phe Val Arg Asn Leu Asn Gly Trp Tyr Tyr
             20                  25                  30

Asp Val Lys Leu Arg Arg Lys Glu His Pro Leu Pro Pro Gly Asp Met
         35                  40                  45

Gly Trp Pro Leu Ile Gly Asn Leu Leu Ser Phe Ile Lys Asp Phe Ser
 50                  55                  60

Ser Asp His Pro Asp Ser Phe Ile Asn Asn Leu Val Leu Lys Tyr Gly
 65                  70                  75                  80

Arg Ser Gly Ile Tyr Lys Thr His Leu Phe Gly Asn Pro Ser Ile Ile
                 85                  90                  95

Val Cys Glu Pro Gln Met Cys Arg Val Leu Thr Asp Val Asn
            100                 105                 110

Phe Lys Leu Gly Tyr Pro Lys Ser Ile Lys Glu Leu Ala Arg Cys Arg
            115                 120                 125

Pro Met Ile Asp Val Ser Asn Ala Glu His Arg Leu Phe Arg Arg Leu
        130                 135                 140

Ile Thr Ser Pro Ile Val Gly His Lys Ala Leu Ala Met Tyr Leu Glu
145                 150                 155                 160

Arg Leu Glu Glu Ile Val Ile Asn Ser Leu Glu Glu Leu Ser Ser Met
                165                 170                 175

Lys His Pro Val Glu Leu Leu Lys Glu Met Lys Lys Val Ser Phe Lys
            180                 185                 190

Ala Ile Val His Val Phe Met Gly Ser Ser Asn Gln Asp Ile Ile Lys
        195                 200                 205

Lys Ile Gly Ser Ser Phe Thr Asp Leu Tyr Asn Gly Met Phe Ser Ile
210                 215                 220

Pro Ile Asn Val Pro Gly Phe Thr Phe His Lys Ala Leu Glu Ala Arg
225                 230                 235                 240

Lys Lys Leu Ala Lys Ile Val Gln Pro Val Val Asp Glu Arg Arg Leu
                245                 250                 255

Met Ile Glu Asn Gly Pro Gln Glu Gly Ser Gln Arg Lys Asp Leu Ile
            260                 265                 270

Asp Ile Leu Leu Glu Val Lys Asp Glu Asn Gly Arg Lys Leu Glu Asp
        275                 280                 285

Glu Asp Ile Ser Asp Leu Leu Ile Gly Leu Leu Phe Ala Gly His Glu
290                 295                 300

Ser Thr Ala Thr Ser Leu Met Trp Ser Ile Thr Tyr Leu Thr Gln His
305                 310                 315                 320

Pro His Ile Leu Lys Lys Ala Lys Glu Glu Gln Glu Glu Ile Thr Arg
                325                 330                 335

Thr Arg Phe Ser Ser Gln Lys Gln Leu Ser Leu Lys Gly Ile Lys Gln
            340                 345                 350

Met Val Tyr Leu Ser Gln Val Ile Asp Glu Thr Leu Arg Cys Ala Asn
        355                 360                 365

Ile Ala Phe Ala Thr Phe Arg Glu Ala Thr Ala Asp Val Asn Ile Asn
        370                 375                 380

Gly Tyr Ile Ile Pro Lys Gly Trp Arg Val Leu Ile Trp Ala Arg Ala
385                 390                 395                 400

Ile His Met Asp Ser Glu Tyr Tyr Pro Asn Pro Glu Phe Asn Pro
                405                 410                 415

Ser Arg Trp Asp Asp Tyr Asn Ala Lys Ala Gly Thr Phe Leu Pro Phe
                420                 425                 430
```

Gly Ala Gly Ser Arg Leu Cys Pro Gly Ala Asp Leu Ala Lys Leu Glu
        435                 440                 445

Ile Ser Ile Phe Leu His Tyr Phe Leu Leu Asn Tyr Arg Leu Glu Arg
    450                 455                 460

Ile Asn Pro Glu Cys His Val Thr Ser Leu Pro Val Ser Lys Pro Thr
465                 470                 475                 480

Asp Asn Cys Leu Ala Lys Val Ile Lys Val Ser Cys Ala
                485                 490

<210> SEQ ID NO 3
<211> LENGTH: 1482
<212> TYPE: DNA
<213> ORGANISM: Glycyrrhiza uralensis

<400> SEQUENCE: 3
atggaagtac attgggtttg catgtccgct gccactttgt tggtatgcta cattttttgga     60 agcaagtttg tgaggaattt gaatgggtgg tattatgatg taaaactaag aaggaaagaa    120
cacccactac ccccaggtga catgggatgg cctcttatcg gcgatctatt gtccttcatc    180
aaagatttct catcgggtca ccctgattca ttcatcaaca accttgttct caaatatgga    240
cgaagtggta tctacaagac tcacttgttt gggaatccaa gcatcattgt ttgtgagcct    300
cagatgtgta ggcgagttct cactgatgat gtgaacttta gcttggtta ccaaaatct     360 atcaaagagt tggcacgatg tagacccatg attgatgtct ctaatgcgga acataggctt    420
tttcgacgcc tcattacttc cccaatcgtg ggtcacaagg cgctagcaat gtacctagag    480
cgtcttgagg aaattgtgat caattcgttg aagaattgt ccagcatgaa gcaccccgtt     540
gagctcttga agagatgaa gaaggtttcc tttaaagcca ttgtccacgt cttcatgggc      600
tcttccaatc aggacatcat taaaaaaatt ggaagttcgt ttactgattt gtacaatggc    660
atgttctcta tccccattaa cgtacctggt tttacattcc acaaagcact cgaggcacgt    720
aagaagctag ccaaaatagt tcaacccgtt gtggatgaaa ggcggttgat gatagaaaat    780
ggtccacaag aagggagcca agaaaaagat cttattgata ttcttttgga agtcaaagat    840
gagaatggac gaaaattgga ggacgaggat attagcgatt tattaatagg cttttgttc    900 gctggccatg aaagtacagc aaccagttta atgtggtcaa ttacgtatct tacacagcat    960 cccccatatct tgaaaaaggc taaggaagag caggaagaaa taacgaggac aagattttcc   1020
tcgcagaaac aattaagtct taaggaaatt aagcaaatgg tttatctttc tcaggtaatt   1080
gatgaaactt tacgatgtgc caatattgcc tttgcaactt ttcgagaggc aactgctgat   1140
gtgaacatca atggttatat cataccaaag ggatggagag tgctaatttg gcaagagcc    1200 attcatatgg attctgaata ttacccaaat ccagaagaat ttaatccatc gagatgggat   1260
gattacaatg ccaaagcagg aaccttcctt ccttttggag caggaagtag actttgtcct   1320
ggagccgact ggcgaaaact tgaaatttcc atatttcttc attatttcct ccgtaattac   1380
aggttggaga gaataaatcc agaatgtcac gttaccagct taccagtatc taaacccaca   1440
gacaattgtc tcgctaaggt gataaaggtt tcatgtgctt ag                     1482

<210> SEQ ID NO 4
<211> LENGTH: 1482
<212> TYPE: DNA
<213> ORGANISM: Glycyrrhiza uralensis

<400> SEQUENCE: 4
atggaagtac attgggtttg catgtcgct gccactttgt tggtatgcta cattttttgga     60 agcaagtttg tgaggaattt gaatgggtgg tattatgatg taaaactaag aaggaaagaa    120
cacccactac ccccaggtga catgggatgg cctcttatcg gcaatctatt gtccttcatc    180
aaagatttct catcggatca ccctgattca ttcatcaaca accttgttct caaatatgga    240
cgaagtggta tctacaagac tcacttgttt gggaatccaa gcatcattgt ttgcgagcct    300
cagatgtgta ggcgagttct cactgatgat gtgaacttta agcttggtta tccaaaatct    360
atcaaagagt tggcacgatg tagacccatg attgatgtct ctaatgcgga acataggctt    420
tttcgacgcc tcattacttc cccaatcgtg ggtcacaagg cgctagcaat gtacctagaa    480
cgtcttgagg aaattgtgat caattcgttg gaagaattgt ccagcatgaa gcaccccgtt    540
gagctcttga agagatgaa gaaggtttcc tttaaagcca ttgtccacgt tttcatgggc    600
tcttccaatc aggacatcat taaaaaaatt ggaagttcgt ttactgattt gtacaatggc    660
atgttctcta tccccattaa cgtacctggt tttacattcc acaaagcact cgaggcacgt    720
aagaagctag ccaaaatagt tcaacccgtt gtggatgaaa ggcggttgat gatagaaaat    780
ggtccacaag aagggagcca agaaaagat cttattgata ttcttttgga agtcaaagat    840
gagaatggac gaaaattgga ggacgaggat attagcgatt tattaatagg gcttttgttt    900
gctggccatg aaagtacagc aaccagttta atgtggtcaa ttacatatct tacacagcat    960
ccccatatct tgaaaaaggc taaggaagag caggaagaaa taacgaggac aagattttcc   1020
tcgcagaaac aattaagtct taaggaaatt aagcaaatgg tttatctttc tcaggtaatt   1080
gatgaaacgt tacgatgtgc caatattgcc tttgcaactt ttcgagaggc aactgctgat   1140
gtgaacatca atggttatat cataccaaag ggatggagag tgctaatttg ggcaagagcc   1200
attcatatgg attctgaata ttacccaaat ccagaagaat ttaatccatc gagatgggat   1260
gattacaatg ccaaagcagg aaccttcctt ccttttggag caggaagtag actttgtcct   1320
ggagccgact ggcgaaaact tgaaatttcc atatttcttc attatttcct ccttaattac   1380
aggttggaga gaataaatcc agaatgtcac gttaccagct taccagtatc taagcccaca   1440
gacaattgtc tcgctaaggt gataaaggtt tcatgtgctt ag                      1482

<210> SEQ ID NO 5
<211> LENGTH: 31
<212> TYPE: DNA
<213> ORGANISM: Artificial
<220> FEATURE:
<223> OTHER INFORMATION: primer

<400> SEQUENCE: 5
caccatggaa gtacattggg tttgcatgtc c                                   31

<210> SEQ ID NO 6
<211> LENGTH: 26
<212> TYPE: DNA
<213> ORGANISM: Artificial
<220> FEATURE:
<223> OTHER INFORMATION: primer

<400> SEQUENCE: 6
ctaagcacat gaaaccttta tcacct                                         26

<210> SEQ ID NO 7
<211> LENGTH: 44
<212> TYPE: DNA
<213> ORGANISM: Artificial
<220> FEATURE:

<223> OTHER INFORMATION: primer

<400> SEQUENCE: 7
gggcggccgc actagtatcg atggaagaat caagctccat gaag                44

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
ttaattaatc accatacatc acgcaaatac                                30

<210> SEQ ID NO 9
<211> LENGTH: 45
<212> TYPE: DNA
<213> ORGANISM: Artificial
<220> FEATURE:
<223> OTHER INFORMATION: primer

<400> SEQUENCE: 9
ggatgatcca ctagtggatc ctctagctcc ctaacatgta ggtgg               45

<210> SEQ ID NO 10
<211> LENGTH: 45
<212> TYPE: DNA
<213> ORGANISM: Artificial
<220> FEATURE:
<223> OTHER INFORMATION: primer

<400> SEQUENCE: 10
taatgcaggg ccgcaggatc cgtgtggaag aacgattaca acagg               45

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tgcggccctg cattaatgaa tcggccaacg                                30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
actagtggat catccccacg cgccctgtag                                30

<210> SEQ ID NO 13
<211> LENGTH: 493
<212> TYPE: PRT
<213> ORGANISM: Glycyrrhiza glabra

<400> SEQUENCE: 13

Met Glu Val His Trp Val Cys Met Ser Ala Ala Thr Leu Leu Val Cys
1               5                   10                  15

Tyr Ile Phe Gly Ser Lys Phe Val Arg Asn Leu Asn Gly Trp Tyr Tyr
            20                  25                  30

-continued

```
Asp Val Lys Leu Arg Arg Lys Glu His Pro Leu Pro Pro Gly Asp Met
         35                  40                  45
Gly Trp Pro Leu Ile Gly Asn Leu Leu Ser Phe Ile Lys His Phe Ser
             50                  55                  60
Ser Gly His Pro Asp Ser Phe Ile Asn Asn Leu Val Leu Lys Tyr Gly
 65                  70                  75                  80
Arg Ser Gly Ile Tyr Lys Thr His Leu Phe Gly Asn Pro Ser Ile Ile
                 85                  90                  95
Ala Cys Glu Pro Gln Met Cys Arg Arg Val Leu Thr Asp Asp Val Asn
                100                 105                 110
Phe Lys Leu Gly Tyr Pro Lys Ser Ile Lys Glu Leu Ala Arg Cys Arg
            115                 120                 125
Pro Met Ile Asp Val Ser Asn Ala Glu His Arg His Phe Arg Arg Leu
        130                 135                 140
Ile Thr Ser Pro Ile Val Gly His Lys Ala Leu Ala Met Tyr Leu Glu
145                 150                 155                 160
Arg Leu Glu Glu Ile Val Ile Asn Ser Leu Glu Leu Ser Ser Thr
                165                 170                 175
Lys His Pro Val Glu Leu Leu Lys Glu Met Lys Lys Val Ser Phe Lys
            180                 185                 190
Ala Ile Val His Val Phe Met Gly Ser Ser Asn Gln Asp Ile Ile Lys
        195                 200                 205
Lys Ile Gly Ser Ser Phe Thr Asp Leu Tyr Asn Gly Met Phe Ser Ile
    210                 215                 220
Pro Ile Asn Val Pro Gly Phe Thr Phe His Lys Ala Leu Glu Ala Arg
225                 230                 235                 240
Lys Lys Leu Ala Lys Ile Val Gln Pro Val Val Asp Glu Arg Arg Leu
                245                 250                 255
Met Ile Glu Asn Gly Pro Gln Glu Gly Ser Gln Arg Lys Asp Leu Ile
            260                 265                 270
Asp Ile Leu Leu Glu Val Lys Asp Glu Asn Gly Arg Lys Leu Glu Asp
        275                 280                 285
Glu Asp Ile Ser Asp Leu Leu Ile Gly Leu Leu Phe Ala Gly His Glu
    290                 295                 300
Ser Thr Ala Thr Gly Leu Met Trp Ser Ile Thr Tyr Leu Thr Gln His
305                 310                 315                 320
Pro His Ile Leu Lys Lys Ala Lys Glu Glu Gln Glu Glu Ile Thr Arg
                325                 330                 335
Thr Arg Phe Ser Ser Gln Lys Gln Leu Ser Leu Lys Glu Ile Lys Gln
            340                 345                 350
Met Val Tyr Leu Ser Gln Val Ile Asp Glu Thr Leu Arg Cys Ala Asn
        355                 360                 365
Ile Ala Phe Ala Thr Phe Arg Glu Ala Thr Ala Asp Val Asn Ile Asn
    370                 375                 380
Gly Tyr Ile Ile Pro Lys Gly Trp Arg Val Leu Ile Trp Ala Arg Ala
385                 390                 395                 400
Ile His Met Asp Ser Glu Tyr Tyr Pro Asn Pro Glu Glu Phe Asn Pro
                405                 410                 415
Ser Arg Trp Asp Asp Tyr Asn Ala Lys Ala Gly Thr Phe Leu Pro Phe
            420                 425                 430
Gly Ala Gly Ser Arg Leu Cys Pro Gly Ala Asp Leu Ala Lys Leu Glu
        435                 440                 445
```

```
Ile Ser Ile Phe Leu His Tyr Phe Leu Leu Asn Tyr Arg Leu Glu Arg
        450                 455                 460

Ile Asn Pro Glu Cys His Val Thr Ser Leu Pro Val Ser Lys Pro Thr
465                 470                 475                 480

Asp Asn Cys Leu Ala Lys Val Ile Lys Val Ser Cys Ala
                485                 490
```

<210> SEQ ID NO 14
<211> LENGTH: 1482
<212> TYPE: DNA
<213> ORGANISM: Glycyrrhiza glabra

<400> SEQUENCE: 14

```
atggaagtac attgggtttg catgtccgct gccactttgt tggtatgcta cattttttgga      60 agcaagtttg tgaggaattt gaatgggtgg tattatgatg taaaactaag aaggaaagaa     120
cacccactac ccccaggtga catgggatgg cctcttatcg gcaatctatt gtccttcatc     180
aaacatttct catcgggtca ccctgattca ttcatcaaca accttgttct caaatatgga     240
cgaagtggta tctacaagac tcacttgttt gggaatccaa gcatcattgc ttgtgagcct     300
cagatgtgta ggcgagtgct cactgatgat gtgaacttta gcttggttta tccaaaatct     360
atcaaagagt tggcacgatg tagacccatg attgatgtct ctaatgcgga acataggcac     420
tttcgacgcc tcattacttc cccaatcgtg ggtcacaagg cgctagcaat gtacctagaa     480
cgtcttgagg aaattgtgat caattcgttg aagaattgt  ccagcacgaa  gcacccgtt    540 gagctcttga agagatgaa gaaggtttcc tttaaagcca ttgtccacgt cttcatgggc     600
tcttccaatc aggacatcat taaaaaaatt ggaagtcgt ttactgattt gtacaatggc     660
atgttctcca tccccattaa cgtacctggt tttacattcc acaaagcact cgaggcacgt     720
aagaagctag ccaaaatagt tcaacccgtt gtggatgaaa ggcggttgat gatagaaaat     780
ggtccacaag aagggagcca agaaaaagat cttattgata ttcttttgga agtcaaagat     840
gagaatggac gaaaattgga ggacgaggat attagcgatt tattaatagg cttttgttc     900 gctggccacg aaagtacagc aaccggttta atgtggtcaa ttacatatct tacacagcat     960
ccccatatct tgaaaaaggc taaggaagag caggaagaaa taacgaggac aagatttttcc    1020 tcgcagaaac aattaagtct taaggaaatt aagcaaatgg tttatctttc tcaggtaatt    1080
gatgaaactt tacgatgtgc caatattgcc tttgcaactt ttcgagaggc aactgctgat    1140
gtgaacatca atggttatat cataccaaag ggatggagag tgctaatttg gcaagagcc     1200 attcatatgg attctgaata ttacccaaat ccagaagaat ttaatccatc gagatgggat    1260
gattacaatg ccaaagcagg aaccttcctt ccttttggag caggaagtag actttgtcct    1320
ggagccgact tggcgaaact tgaaatttcc atatttcttc attatttcct ccttaattac    1380
aggttggaga gaataaatcc agaatgtcac gttaccagct taccagtatc taagcccaca    1440
gacaattgtc tcgctaaggt gataaaggtt tcatgtgctt ag                       1482
```